(12) United States Patent
Wagner et al.

(10) Patent No.: US 6,475,808 B1
(45) Date of Patent: Nov. 5, 2002

(54) ARRAYS OF PROTEINS AND METHODS OF USE THEREOF

(75) Inventors: Peter Wagner, Belmont; Dana Ault-Riche, Palo Alto; Steffen Nock, Redwood City; Christian Itin, Menlo Park, all of CA (US)

(73) Assignee: Zyomyx, Incorporated, Hayward, CA (US)

( * ) Notice: Subject to any disclaimer, the term of this patent is extended or adjusted under 35 U.S.C. 154(b) by 0 days.

(21) Appl. No.: 09/353,215

(22) Filed: Jul. 14, 1999

Related U.S. Application Data

(63) Continuation-in-part of application No. 09/115,455, filed on Jul. 14, 1998.

(51) Int. Cl.$^7$ ............................................. G01N 33/543
(52) U.S. Cl. ..................... 436/518; 422/57; 427/134; 427/261; 427/287; 427/387; 427/407.2; 427/518; 435/7.1; 435/287.1; 435/287.9; 435/288.3; 435/288.4; 436/524; 436/525; 436/527; 436/528; 436/532; 436/533; 436/535; 436/536
(58) Field of Search ............................ 435/287.9, 286.1, 435/287.1, 288.3, 288.4, 7.1; 427/261, 287, 387, 407.2, 134, 518, 487.2; 436/518, 524, 525, 527, 528, 532, 533, 535, 536; 422/57

(56) References Cited

U.S. PATENT DOCUMENTS

| | | | |
|---|---|---|---|
| 4,071,409 A | * | 1/1978 | Messing et al. ............... 195/63 |
| 4,562,157 A | | 12/1985 | Lowe et al. ................. 435/291 |
| 4,690,715 A | | 9/1987 | Allara et al. ............... 148/6.15 |
| 4,722,896 A | | 2/1988 | Kadish et al. |
| 4,908,112 A | | 3/1990 | Pace ........................... 204/299 |
| 4,973,493 A | | 11/1990 | Guire ............................ 427/2 |
| 4,987,032 A | | 1/1991 | Tsutomu et al. |
| 5,079,600 A | | 1/1992 | Schnur et al. ................ 357/4 |
| 5,096,807 A | * | 3/1992 | Leaback ........................ 435/6 |
| 5,143,854 A | * | 9/1992 | Pirrung et al. .............. 436/518 |
| 5,154,808 A | | 10/1992 | Tsutomu et al. |
| 5,160,597 A | | 11/1992 | Colapicchioni et al. ..... 204/403 |

(List continued on next page.)

FOREIGN PATENT DOCUMENTS

| | | |
|---|---|---|
| EP | 596421A 1 | 10/1993 |
| EP | 780423A 2 | 12/1996 |
| WO | WO 91/16425 | 10/1991 |
| WO | WO 93/21528 | 10/1993 |
| WO | WO 95/08770 | 3/1995 |

(List continued on next page.)

OTHER PUBLICATIONS

Cha, et al., "Expression of fused protein, human interleukin–2 and green fluorescent protein, in insect larvae" *Annual Meeting of The American Institute of Chemical Engineers*, Los Angeles , CA (1997).

(List continued on next page.)

*Primary Examiner*—Christopher L. Chin
(74) *Attorney, Agent, or Firm*—Alicia J. Hager; Gregory L. Heinkel

(57) ABSTRACT

Protein arrays for the parallel, in vitro screening of biomolecular activity are provided. Methods of using the protein arrays are also disclosed. On the arrays, a plurality of different proteins, such as different members of a single protein family, are immobilized on one or more organic thinfilms on the substrate surface. The protein arrays are particularly useful in drug development, proteomics, and clinical diagnostics.

3 Claims, 8 Drawing Sheets

U.S. PATENT DOCUMENTS

| | | | |
|---|---|---|---|
| 5,242,828 A | 9/1993 | Bergstrom et al. | 435/291 |
| 5,252,743 A * | 10/1993 | Barrett et al. | 548/303.7 |
| 5,294,369 A | 3/1994 | Shigekawa et al. | 252/313.1 |
| 5,296,114 A | 3/1994 | Manz | |
| 5,304,487 A | 4/1994 | Wilding et al. | |
| 5,342,692 A | 8/1994 | Ribi | 428/420 |
| 5,384,261 A | 1/1995 | Winkler et al. | 436/518 |
| 5,405,766 A * | 4/1995 | Kallury et al. | 435/174 |
| 5,405,783 A * | 4/1995 | Pirrung et al. | 436/518 |
| 5,412,087 A | 5/1995 | Foder et al. | |
| 5,429,708 A | 7/1995 | Linford et al. | 216/66 |
| 5,441,876 A | 8/1995 | Singh | |
| 5,445,934 A | 8/1995 | Fodor et al. | 435/6 |
| 5,472,881 A | 12/1995 | Beebe et al. | 436/94 |
| 5,510,270 A * | 4/1996 | Fodor et al. | 436/518 |
| 5,512,131 A | 4/1996 | Kumar et al. | 156/655.1 |
| 5,512,492 A | 4/1996 | Herron et al. | 436/518 |
| 5,514,501 A | 5/1996 | Tarlov | 430/5 |
| 5,520,787 A | 5/1996 | Hanagan et al. | 204/409 |
| 5,571,410 A | 11/1996 | Swedberg et al. | 210/198.2 |
| 5,593,838 A | 1/1997 | Zanzucchi et al. | 435/6 |
| 5,603,351 A | 2/1997 | Cherukuri et al. | 137/597 |
| 5,605,662 A | 2/1997 | Heller et al. | 422/68.1 |
| 5,620,850 A * | 4/1997 | Bamdad et al. | 530/300 |
| 5,622,826 A | 4/1997 | Varma | 435/6 |
| 5,624,711 A * | 4/1997 | Sundberg et al. | 427/261 |
| 5,629,213 A * | 5/1997 | Kornguth et al. | 436/518 |
| 5,635,358 A | 6/1997 | Wilding et al. | 435/7.2 |
| 5,637,469 A | 6/1997 | Wilding | 435/7.21 |
| 5,677,195 A | 10/1997 | Winkler et al. | 436/518 |
| 5,677,196 A | 10/1997 | Janatova et al. | |
| 5,681,484 A | 10/1997 | Zanzucchi et al. | 216/2 |
| 5,688,642 A | 11/1997 | Chrisey et al. | 435/6 |
| 5,700,642 A | 12/1997 | Monforte et al. | 435/6 |
| 5,719,060 A | 2/1998 | Hutchens et al. | 436/174 |
| 5,726,026 A | 3/1998 | Wilding et al. | |
| 5,731,152 A | 3/1998 | Maracas et al. | 3/98 |
| 5,744,305 A | 4/1998 | Fodor et al. | |
| 5,766,908 A | 6/1998 | Klein et al. | |
| 5,776,674 A | 7/1998 | Ulmer | |
| 5,837,832 A * | 11/1998 | Chee et al. | 536/22.1 |
| 5,843,767 A * | 12/1998 | Beattie | 435/287.1 |
| 5,858,188 A | 1/1999 | Soane et al. | |
| 5,861,242 A * | 1/1999 | Chee et al. | 435/5 |
| 5,866,345 A | 2/1999 | Wilding et al. | |
| 5,919,523 A | 7/1999 | Sundberg et al. | |
| 5,925,552 A * | 7/1999 | Keogh et al. | 435/174 |
| 5,928,880 A | 7/1999 | Wilding et al. | |
| 5,942,443 A | 8/1999 | Parce et al. | |

FOREIGN PATENT DOCUMENTS

| | | |
|---|---|---|
| WO | WO 95/35505 | 12/1995 |
| WO | WO9535505 | 12/1995 |
| WO | WO 96/02830 | 2/1996 |
| WO | WO 96/10178 | 4/1996 |
| WO | WO 96/26432 | 8/1996 |
| WO | WO 96/29629 | 9/1996 |
| WO | WO 96/38726 | 12/1996 |
| WO | WO 96/39937 | 12/1996 |
| WO | WO 97/07429 | 2/1997 |
| WO | WO 97/21094 | 6/1997 |
| WO | WO 97/33737 | 9/1997 |
| WO | WO 97/36681 | 10/1997 |
| WO | WO 97/41424 | 11/1997 |
| WO | WO 97/41425 | 11/1997 |
| WO | WO9823948 | 6/1998 |
| WO | WO 98/23948 | 6/1998 |
| WO | WO9839481 | 9/1998 |
| WO | WO9843086 | 10/1998 |
| WO | WO 98/50773 | 11/1998 |
| WO | WO9850773 | 11/1998 |
| WO | WO 99/40434 | 8/1999 |
| WO | WO 00/52209 | 9/2000 |
| WO | WO 00/53625 | 9/2000 |
| WO | WO 00/54046 | 9/2000 |

OTHER PUBLICATIONS

Mauracher, et al., "Reduction of rubella ELISA background using heat denatured sample buffer" *J. Immunol. Methods* 145:251–254 (1991).

Memeny, "Enzyme–linked immunoassays" *Immuno–Chemistry 1* Johnstone and Turner (eds.) pp. 147–175 (1997).

Becker et al. "Fabrication of microstructures with high aspect ratios and great structural heights by synchrotron radiation lithography, galvanoforming, and plastic moulding (LIGA process)" *Microelectronic Engineering* 4:35–56 (1986).

Becker et al. "Production of separation –nozzle systems for uranium enrichment by a combination of x–ray lithography and glavanoplastics" *Naturwissenschaften* 69:520–523 (1982).

Condra et al. "In vivo emergence of HIV–1 variants resistant to multiple protease inhibitors" *Nature* 374:569–571 (1995).

Dzgoev et al "Microformat imaging ELISA for pesticide determination" *Anal. Chem.* 68(19):3364 (1996).

Ekins "Ligand assays from electrophoresis to miniaturized microarrays" *Clin. Chem.* 44(9):2015–2030 (1998).

Elkins et al. "Multianalyte microspote immunoassay–microanalytical "compact disk" of the future" *Clin. Chem.* 37(11):1955–1967 (1991).

Geohegan et al. "Fluorescence–based continuous assay for the aspartyl protease of human immunodeficiency virus–1" *FEBS* 262:119–122 (1990).

Ho et al. "Characterization of human immunodeficiency virus type 1 variants that encode viral proteases with decreased sensitifity to an inhibitor of the viral protease" *Journal of Virology* 68:2016–2020 (1994).

Jacobson et al. "Fused quartz substrates for microchip electrophoresis" *Anal. Chem.* 67:2059–2063.

Jones et al. "Microminiaturized immunoassays using atomic force microscopy and compositionally patterned antigen arrays" *Anal. Chem.* 70(7):1223–1241 (1998).

Kaplan et al. "Selection of multiple human immunodeficiency virus type 1 variants that encode viral proteaes with decreased sensitivity to an inhibitor of the viral inhibitor" *Proc. Natl. Acad. Sci. USA* 91:5597–5601 (1994).

Korant et al. "The HIV protease and therapies for aids" Adv. in Experimental Med. and Biol 421:279–284 (1997).

Kricka "Miniaturization of analytical systems" *Clin. Chem.* 44(9):2008–2014 (1998).

Loeb et al. "Complete mutegenesis of the HIV–1 protease" *Nature* 340:397–400 (1989).

Louis et al. "Autoprocessing of the HIV–1 protease using purified wild–type and mutated fusion proteins expressed at high levels in *Eschericia coli*" *Eur. J. Biochem.* 199:361–369 (1991).

Marks et al. "By–passing immunication– Human antibodies from V–gene libraries displayed on phage" *J. Mol. Biol.* 222:581–597 (1991).

Martynova et al. "Fabricating of plastic microfluid channels by imprinting methods" *Anal. Chem.* 69:4783–47–89 (1997).

Moore et al. "Peptide substrates and indibitors of HIV–1 protease" *Biochem. Biophys. Res. Com.* 159:420–425 (1989).

Roberts et al. "Rationale design of peptide–based HIV proteinase inhibitors" *Science* 248:358–361 (1990).

Rowe et al. "Array biosensor for simultaneous identification of bacterial, viral and protein analytes" *Anal. Chem.* 71(17):3846–3852 (1999).

Schock et al. "Mutaional anatomy of an HIV–1 protease variant conferring cross–resistance to protease inhibitors in clinical trials" *J. Biol. Chem.* 271:31957–31963 (1996).

Silzel et al. "Mass–sensing, multianalyte microarray immunoassay with imaging detection" *Clin. Chem.* 44(9):2036–2043 (1998).

Skalka: Retroviral proteases: first glimpses at the anatomy of a processing machine *Cell* 56:911–913 (1989).

Sundberg et al. "Spatially–addressable immobiliaztion of macromolecules on solid supports" *J. Am. Chem. Soc.* 117:12050–12057 (1995).

Wondrak et al. "Influence of flanking sequences on the dimer stability of human immunodeficiency virus type 1 protease" *Biochemistry* 35:12957–12962 (1996).

Wu et al. "Structural basis for specificity of retroviral proteases" Biochemistry 37:4518–4526 (1998).

Pham, et al. "Human Interleukin–2 Production in Insect (*Trichoplusia ni*) Larvae: Effects and Partial Control of Proteolysis", *Biotechnology and Bioengineering* vol. 62(2) pp. 175–182; Jan. 20, 1999.

Pale–Grosdemange et al. (1991). Formation of self–assembled monolayers by chemisorption of derivatives of oligo(ethylene glycol) of structure HS(CH2)11(OCH2CH2)mOH on gold. J. Am. Chem. Soc. 113(1):12–20.*

Nock et al. (1997). Reversible, site–specific immobilizationi of polyarginine–tagged fusion proteins on mica surfaces. FEBS Letters. 414:233–238.*

Collioud et al. (1993). Oriented and covalent immobilization of target molecules to solid supports: Synthesis and application of a light–activatable and thiol–reactive cross–linking reagent. Bioconjugate Chem. 4:528–536.*

Sigal et al. (1996). A self–assembled monolayer for the binding and study of histidine–tagged proteins by surface plasmon resonance. Anal. Chem. 38:490–497.*

Cload et al.,"Development of improved tRNAs for in vitro biosynthesis of proteins containing unnatural amino acids," *Chemistry and Biology*, 3:1033–1038 (1996).

Dammer et al., "Specific antigen/antibody interactions measured by force microscopy," *Biophysical Journal*, 70:2437–2441 (1996).

Dawson et al., "Peptide–derived self–assembled monolayers: adsorption of N–stearoyl I–Cysteine methyl ester on gold," *Journal of Molecular Recognition*, 10:18–25 (1997).

Duschl et al., "Surface engineering: optimization of antigen presentation in self–assembled monolayers," *Biophysical Journal*, 70:1985–1995 (1996).

Ellman et al., "Biosynthetic method for introducing unnatural amino acids site–specifically into proteins," *Methods in Enzymology*, 202:301–337 (1991).

Hegner et al., "Ultralarge atomically flat template–stripped Au surfaces for scanning probe microscopy," *Surface Science*, 291:39–46 (1993).

Hegner et al., "Immobilizing DNA on gold via thiol modification for atomic force microscopy imaging in buffer solutions," *FEBS*, 336(3):452–456 (1993).

Hegner et al., "Modified DNA immobilized on bioreactive self–assembled monolayer on gold for dynamic force microscopy imaging in aqueous buffer solution," *J. Vac. Sci. Technol. B*, 14(2):1418–1421 (1996).

Hochuli et al., "Genetic approach to facilitate purification of recombinant proteins with a novel metal chelate adsorbent," *Biotechnology*, 6:1321–1325 (1988).

Lemmo et al., "Characterization of inkjet chemical microdispenser for combinatorial library synthesis," *Anal. Chem.*, 69:543–551 (1997).

Linford et al., "Alkyl monolayers on silicon prepared from 1–alkenes and hydrogen–terminated silicon," *J. Am. Chem. Soc.*, 117:3145–3155 (1995).

Mrksich et al., "Controlling cell attachment on contoured surfaces with self–assembled monolayers of alkanethiolates on gold," *Proc. Natl. Acad. Sci. USA*, 93:10775–10778 (1996).

Nock, "Reversible, site–specific immobilization of polyarginine–taggeed fusio proteins on mica surfaces," *FEBS*, 414:233–238 (1997).

Noren et al., "A general method for site–specific incorporation of unnatural amino acids into proteins," *Science*, 244:182–188 (1989).

Prime et al., "Self–assembled organic monolayers: model systems for studying absorption of proteins at surfaces," *Science*, 252:1164–1167 (1991).

Singhvi et al., "Engineering cell shape and function," *Science*, 264:696–698 (1994).

Stennicke et al., "Biochemical characteristics of caspases–3, –6, –7 and –8," *The Journal of Biological Chemistry*, 272:25719–25723 (1997).

Sundberg et al., "Spatially–addressable immobilization of macromolecules on solid supports," *J. Am. Chem. Soc.*, 117:12050–12057 (1995).

Talanian et al., "Substrate specificities of caspase family proteases," *The Journal of Biological Chemistry*, 272:9677–9682 (1997).

Thornberry, "Interleukin–1β converting enzyme," *Methods in Enzymology*, 244:615–631 (1994).

Villa et al., "Caspases and caspase inhibitors," *TIBS*, 22:388–393 (1997).

Wagner et al., "ω–functionalized self–assembled monolayers chemisorbed on ultraflat Au(111) surfaces for biological scanning probe microscopy in aqueous buffers," *J. Vac. Sci. Technol. B*, 14(2):1466–1471 (1996).

Wagner et al., "Formation and in Situ modification of monolayers chemisorbed on ultraflat template–stripped gold surfaces," *Langmuir*, 11(10):3867–3875 (1995).

Wagner et al., "Bioreactive self–assembled monolayers on hydrogen–passivated Si(111) as a new class of atomically flat substrates for biological scanning probe microscopy," *Journal of Structural Biology*, 119:189–201 (1997).

Wagner et al., "Covalent immobilization of native biomolecules onto Au(111) via N–hydroxysuccinimide ester functionalized self–assembled monolayers for scanning probe microscopy," *Biophysical Journal*, 70:2052–2066 (1996).

Wilson et al., "Structure and mechanism of interleukin–1β converting enzyme," *Nature*, 370:270–275 (1994).

Patent Abstracts of Japan, vol. 015, No. 034 (c–0799), Jan. 28, 1991 & JP 02 272081 A (Fuji Photo Film Co Ltd), Nov. 6, 1990 abstract.

* cited by examiner

A - A:

B - B :

ARRAYS OF PROTEINS AND METHODS OF USE THEREOF

This application is a continuation-in-part application of co-pending application Ser. No. 09/115,455, filed Jul. 14, 1998, which is incorporated herein by reference in its entirety.

BACKGROUND OF THE INVENTION a) Field of the Invention

The present invention relates generally to arrays of proteins and methods for the parallel, in vitro screening of a plurality of protein-analyte interactions. More specifically, the present invention relates to uses of the arrays for drug development, proteomics, and clinical diagnostics.

b) Description of Related Art

A vast number of new drug targets are now being identified using a combination of genomics, bioinformatics, genetics, and high-throughput biochemistry. Genomics provides information on the genetic composition and the activity of an organism's genes. Bioinformatics uses computer algorithms to recognize and predict structural patterns in DNA and proteins, defining families of related genes and proteins. The information gained from the combination of these approaches is expected to greatly boost the number of drug targets (usually, proteins).

The number of chemical compounds available for screening as potential drugs is also growing dramatically due to recent advances in combinatorial chemistry, the production of large numbers of organic compounds through rapid parallel and automated synthesis. The compounds produced in the combinatorial libraries being generated will far outnumber those compounds being prepared by traditional, manual means, natural product extracts, or those in the historical compound files of large pharmaceutical companies.

Both the rapid increase of new drug targets and the availability of vast libraries of chemical compounds creates an enormous demand for new technologies which improve the screening process. Current technological approaches which attempt to address this need include multiwell-plate based screening systems, cell-based screening systems, microfluidics-based screening systems, and screening of soluble targets against solid-phase synthesized drug components.

Automated multiwell formats are the best developed high-throughput screening systems. Automated 96-well plate-based screening systems are the most widely used. The current trend in plate based screening systems is to reduce the volume of the reaction wells further, thereby increasing the density of the wells per plate (96-well to 384-and 1536-well per plate). The reduction in reaction volumes results in increased throughput, dramatically decreased bioreagent costs, and a decrease in the number of plates which need to be managed by automation.

However, although increases in well numbers per plate are desirable for high throughput efficiency, the use of volumes smaller than 1 microliter in the well format generates significant problems with evaporation, dispensing times, protein inactivation, and assay adaptation. Proteins are very sensitive to the physical and chemical properties of the reaction chamber surfaces. Proteins are prone to denaturation at the liquid/solid and liquid/air interfaces. Miniaturization of assays to volumes smaller than 1 microliter increases the surface to volume ratio substantially. (Changing volumes from 1 microliter to 10 nanoliter increases the surface ratio by 460%, leading to increased protein inactivation.) Furthermore, solutions of submicroliter volumes evaporate rapidly, within seconds to a few minutes, when in contact with air. Maintaining microscopic volumes in open systems is therefore very difficult.

Other types of high-throughput assays, such as miniaturized cell-based assays are also being developed. Miniaturized cell-based assays have the potential to generate screening data of superior quality and accuracy, due to their in vivo nature. However, the interaction of drug compounds with proteins other than the desired targets is a serious problem related to this approach which leads to a high rate of false positive results.

Microfluidics-based screening systems that measure in vitro reactions in solution make use of ten to several-hundred micrometer wide channels. Micropumps, electroosmotic flow, integrated valves and mixing devices control liquid movement through the channel network. Microfluidic networks prevent evaporation but, due to the large surface to volume ratio, result in significant protein inactivation. The successful use of microfluidic networks in biomolecule screening remains to be shown.

Drug screening of soluble targets against solid-phase synthesized drug components is intrinsically limited. The surfaces required for solid state organic synthesis are chemically diverse and often cause the inactivation or non-specific binding of proteins, leading to a high rate of false-positive results. Furthermore, the chemical diversity of drug compounds is limited by the combinatorial synthesis approach that is used to generate the compounds at the interface. Another major disadvantage of this approach stems from the limited accessibility of the binding site of the soluble target protein to the immobilized drug candidates.

Miniaturized DNA chip technologies have been developed (for example, see U.S. Pat. Nos. 5,412,087, 5,445,934 and 5,744,305) and are currently being exploited for nucleic acid hybridization assays. However, DNA biochip technology is not transferable to protein arrays because the chemistries and materials used for DNA biochips are not readily transferable to use with proteins. Nucleic acids withstand temperatures up to 100° C., can be dried and re-hydrated without loss of activity, and can be bound directly to organic adhesion layers supported by materials such as glass while maintaining their activity. In contrast, proteins must remain hydrated, kept at ambient temperatures, and are very sensitive to the physical and chemical properties of the support materials. Therefore, maintaining protein activity at the liquid-solid interface requires entirely different immobilization strategies than those used for nucleic acids. Additionally, the proper orientation of the protein at the interface is desirable to ensure accessibility of their active sites with interacting molecules. With miniaturization of the chip and decreased feature sizes the ratio of accessible to non-accessible antibodies becomes increasingly relevant and important.

In addition to the goal of achieving high-throughput screening of compounds against targets to identify potential drug leads, researchers also need to be able to identify highly specific lead compounds early in the drug discovery process. Analyzing a multitude of members of a protein family or forms of a polymorphic protein in parallel (multitarget screening) enables quick identification of highly specific lead compounds. Proteins within a structural family share similar binding sites and catalytic mechanisms. Often, a compound that effectively interferes with the activity of one family member also interferes with other members of the same family. Using standard technology to discover such additional interactions requires a tremendous effort in time and costs and as a consequence is simply not done.

However, cross-reactivity of a drug with related proteins can be the cause of low efficacy or even side effects in patients. For instance, AZT, a major treatment for AIDS, blocks not only viral polymerases, but also human polymerases, causing deleterious side effects. Cross-reactivity with closely related proteins is also a problem with nonsteroidal anti-inflammatory drugs (NSAIDs) and aspirin. These drugs inhibit cyclooxygenase-2, an enzyme which promotes pain and inflammation. However, the same drugs also strongly inhibit a related enzyme, cyclooxygenase-1, that is responsible for keeping the stomach lining and kidneys healthy, leading to common side-effects including stomach irritation.

For the foregoing reasons, there is a need for miniaturized protein arrays and for methods for the parallel, in vitro, screening of the interactions between a plurality of proteins and one or more analytes in a manner that minimizes reagent volumes and protein inactivation problems.

SUMMARY OF THE INVENTION

The present invention is directed to miniaturized protein arrays and methods of use thereof that satisfy the need for parallel, in vitro, screening of the interactions between a plurality of proteins and one or more analytes in a manner that minimizes reagent volumes and protein inactivation problems.

In one embodiment, the present invention provides an array of proteins which comprises a substrate, at least one organic thinfilm on some or all of the substrate surface, and a plurality of patches arranged in discrete, known regions on portions of the substrate surface covered by organic thinfilm, wherein each of said patches comprises a protein immobilized on the underlying organic thinfilm. Preferably, a plurality of different proteins are present on separate patches of the array.

In a second embodiment, the invention provides a method for screening a plurality of proteins for their ability to interact with a component of a sample. The method of this embodiment comprises delivering the sample to the array of proteins of the invention, and detecting, either directly or indirectly, for the interaction of the component with the immobilized protein of each patch.

In a third embodiment, the invention provides a method for screening a plurality of proteins for their ability to bind a particular component of a sample. The method of this embodiment comprises first delivering the sample to the array of proteins of the invention. In a final step, the method comprises detecting, either directly or indirectly, for the presence or amount of the particular component which is retained at each patch. Optionally, the method comprises the additional step of further characterizing the particular component retained at the site of at least one patch.

In an alternative embodiment, the invention provides a method of assaying for protein-protein binding interactions. The first step of the method of this embodiment comprises delivering a sample comprising at least one protein to be assayed for binding to the protein array of the invention. The last step comprises detecting, either directly or indirectly, for the presence or amount of the protein from the sample which is retained at each patch.

In another embodiment of the invention, a method for assaying for a plurality of analytes in a sample is provided which comprises delivering the sample to a protein array, of the invention and detecting for the interaction of the analytes with the immobilized protein at each patch.

In still another embodiment of the invention, an alternative method for assaying for a plurality of analytes in a sample is provided which comprises delivering the fluid sample to a protein array of the invention and detecting either directly or indirectly, for the presence or amount of analyte retained at each patch.

DETAILED DESCRIPTION OF THE INVENTION

Figure 1:
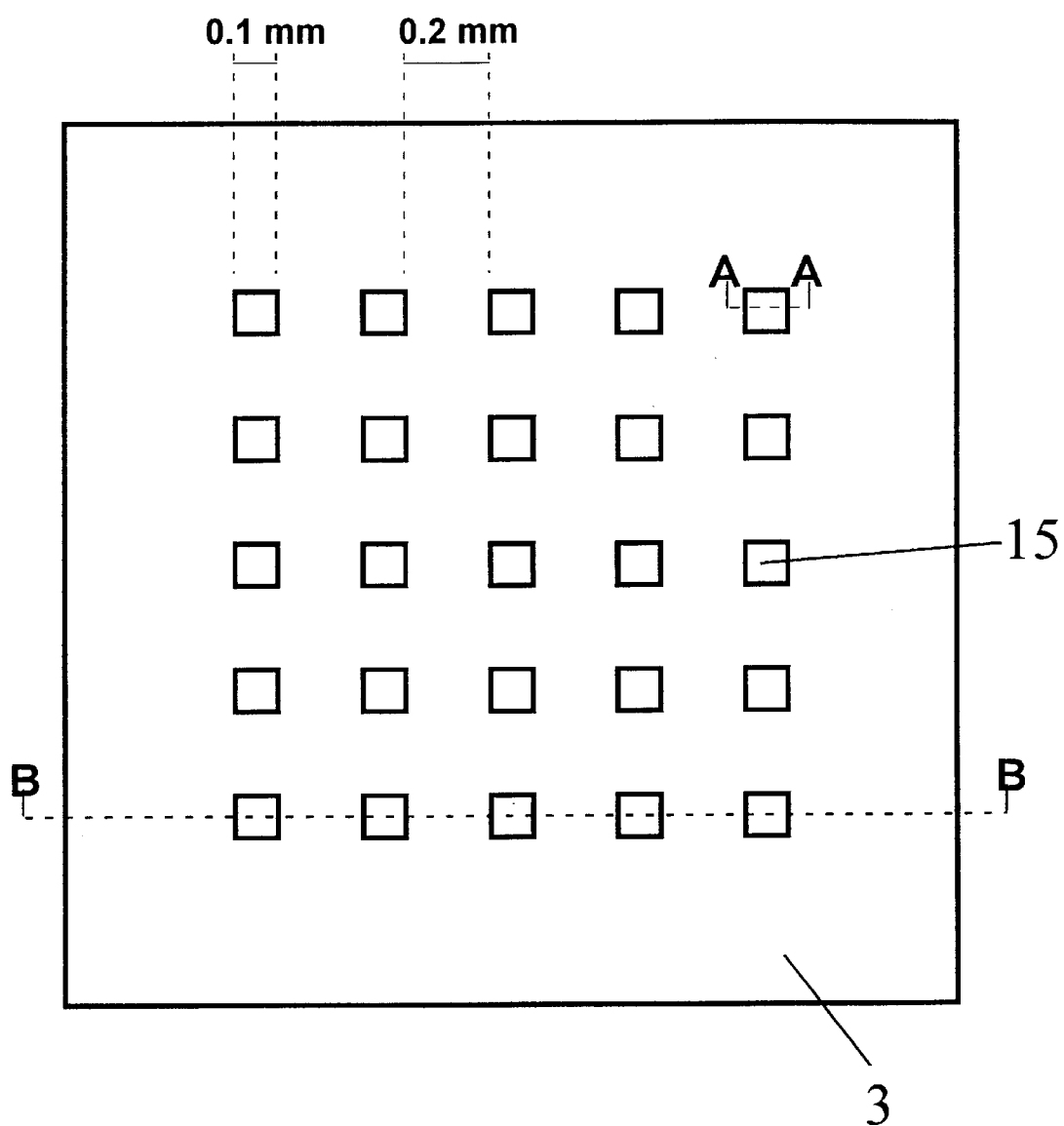
FIG. 1 shows the top view of an array of protein-reactive patches.

A variety of protein arrays, methods, and protein-coated substrates useful for drug development, proteomics, clinical diagnostics, and related applications are provided by the present invention.

(a) Definitions

A "protein" means a polymer of amino acid residues linked together by peptide bonds. The term, as used herein, refers to proteins, polypeptides, and peptides of any size, structure, or function. Typically, however, a protein will be at least six amino acids long. Preferably, if the protein is a short peptide, it will be at least about 10 amino acid residues long. A protein may be naturally occurring, recombinant, or synthetic, or any combination of these. A protein may also be just a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid. An amino acid polymer in which one or more amino acid residues is an "unnatural" amino acid, not corresponding to any naturally occurring amino acid, is also encompassed by the use of the term "protein" herein.

A "fragment of a protein" means a protein which is a portion of another protein. For instance, fragments of a proteins may be polypeptides obtained by digesting full-length protein isolated from cultured cells. A fragment of a protein will typically comprise at least six amino acids. More typically, the fragment will comprise at least ten amino acids. Preferably, the fragment comprises at least about 16 amino acids.

The term "antibody" means an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term "antibody fragment" refers to any derivative of an antibody which is less than full-length. Preferably, the antibody fragment retains at least a significant portion of the full-length antibody's specific binding ability. Examples of antibody fragments include, but are not limited to, Fab, Fab', $F(ab')_2$, scFv, Fv, dsFv diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the $NH_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

"Diabodies" are dimeric scFvs. The components of diabodies typically have shorter peptide linkers than most scFvs and they show a preference for associating as dimers.

An "Fv" fragment is an antibody fragment which consists of one $V_H$ and one $V_L$ domain held together by noncovalent interactions. The term "dsFv" is used herein to refer to an Fv with an engineered intermolecular disulfide bond to stabilize the $V_H$–$V_L$ pair.

A "$F(ab')_2$" fragment is an antibody fragment essentially equivalent to that obtained from immunoglobulins (typically IgG) by digestion with an enzyme pepsin at pH 4.0–4.5. The fragment may be recombinantly produced.

A "Fab'" fragment is an antibody fragment essentially equivalent to that obtained by reduction of the disulfide bridge or bridges joining the two heavy chain pieces in the $F(ab')_2$ fragment. The Fab' fragment may be recombinantly produced.

A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

The term "protein-capture agent" means a molecule or a multi-molecular complex which can bind a protein to itself. Protein-capture agents preferably bind their binding partners in a substantially specific manner. Protein-capture agents with a dissociation constant ($K_D$) of less than about $10^{-6}$ are preferred. Antibodies or antibody fragments are highly suitable as protein-capture agents. Antigens may also serve as protein-capture agents, since they are capable of binding antibodies. A receptor which binds a protein ligand is another example of a possible protein-capture agent. Protein-capture agents are understood not to be limited to agents which only interact with their binding partners through noncovalent interactions. Protein-capture agents may also optionally become covalently attached to the proteins which they bind. For instance, the protein-capture agent may be photocrosslinked to its binding partner following binding.

The term "binding partner" means a protein which is bound by a particular protein-capture agent, preferably in a substantially specific manner. In some cases, the binding partner may be the protein normally bound in vivo by a protein which is a protein-capture agent. In other embodiments, however, the binding partner may be the protein or peptide on which the protein-capture agent was selected (through in vitro or in vivo selection) or raised (as in the case of antibodies). A binding partner may be shared by more than one protein-capture agent. For instance, a binding partner which is bound by a variety of polyclonal antibodies may bear a number of different epitopes. One protein-capture agent may also bind to a multitude of binding partners (for instance, if the binding partners share the same epitope), "Conditions suitable for protein binding" means those conditions (in terms of salt concentration, pH, detergent, protein concentration, temperature, etc.) which allow for binding to occur between a protein and its binding partner in solution. Preferably, the conditions are not so lenient that a significant amount of nonspecific protein binding occurs.

A "body fluid" may be any liquid substance extracted, excreted, or secreted from an organism or tissue of an organism. The body fluid need not necessarily contain cells. Body fluids of relevance to the present invention include, but are not limited to, whole blood, serum, urine, plasma, cerebral spinal fluid, tears, sinovial fluid, and amniotic fluid.

An "array" is an arrangement of entities in a pattern on a substrate. Although the pattern is typically a two-dimensional pattern, the pattern may also be a three-dimensional pattern.

The term "substrate" refers to the bulk, underlying, and core material of the arrays of the invention.

The terms "micromachining" and "microfabrication" both refer to any number of techniques which are useful in the generation of microstructures (structures with feature sizes of sub-millimeter scale). Such technologies include, but are not limited to, laser ablation, electrodeposition, physical and chemical vapor deposition, photolithography, and wet chemical and dry etching. Related technologies such as injection molding and LIGA (x-ray lithography, electrodeposition, and molding) are also included. Most of these techniques were originally developed for use in semiconductors, microelectronics, and Micro-ElectroMechanical Systems (MEMS) but are applicable to the present invention as well.

The term "coating" means a layer that is either naturally or synthetically formed on or applied to the surface of the substrate. For instance, exposure of a substrate, such as silicon, to air results in oxidation of the exposed surface. In the case of a substrate made of silicon, a silicon oxide coating is formed on the surface upon exposure to air. In other instances, the coating is not derived from the substrate and may be placed upon the surface via mechanical, physical, electrical, or chemical means. An example of this type of coating would be a metal coating that is applied to a silicon or polymer substrate or a silicon nitride coating that is applied to a silicon substrate. Although a coating may be of any thickness, typically the coating has a thickness smaller than that of the substrate.

An "interlayer" is an additional coating or layer that is positioned between the first coating and the substrate. Multiple interlayers may optionally be used together. The primary purpose of a typical interlayer is to aid adhesion between the first coating and the substrate. One such example is the use of a titanium or chromium interlayer to help adhere a gold coating to a silicon or glass surface. However, other possible functions of an interlayer are also anticipated. For instance, some interlayers may perform a role in the detection system of the array (such as a semiconductor or metal layer between a nonconductive substrate and a nonconductive coating).

An "organic thinfilm" is a thin layer of organic molecules which has been applied to a substrate or to a coating on a substrate if present. Typically, an organic thinfilm is less than about 20 nm thick. Optionally, an organic thinfilm may be less than about 10 nm thick. An organic thinfilm may be disordered or ordered. For instance, an organic thinfilm can be amorphous (such as a chemisorbed or spin-coated polymer) or highly organized (such as a Langmuir-Blodgett film or self-assembled monolayer). An organic thinfilm may be heterogeneous or homogeneous. Organic thinfilms which are monolayers are preferred. A lipid bilayer or monolayer is a preferred organic thinfilm. Optionally, the organic thinfilm may comprise a combination of more than one form of organic thinfilm. For instance, an organic thinfilm may comprise a lipid bilayer on top of a self-assembled monolayer. A hydrogel may also compose an organic thinfilm. The organic thinfilm will typically have functionalities exposed on its surface which serve to enhance the surface conditions of a substrate or the coating on a substrate in any of a number of ways. For instance, exposed functionalities of the organic thinfilm are typically useful in the binding or covalent immobilization of the proteins to the patches of the array. Alternatively, the organic thinfilm may bear functional groups (such as polyethylene glycol (PEG)) which reduce the non-specific binding of molecules to the surface. Other exposed functionalities serve to tether the thinfilm to the surface of the substrate or the coating. Particular functionalities of the organic thinfilm may also be designed to enable certain detection techniques to be used with the surface. Alternatively, the organic thinfilm may serve the purpose of preventing inactivation of a protein immobilized on a patch of the array or analytes which are proteins from occurring upon contact with the surface of a substrate or a coating on the surface of a substrate.

A "monolayer" is a single-molecule thick organic thinfilm. A monolayer may be disordered or ordered. A monolayer may optionally be a polymeric compound, such as a polynonionic polymer, a polyionic polymer, or a block-copolymer. For instance, the monolayer may be composed of a poly(amino acid) such as polylysine. A monolayer which is a self-assembled monolayer, however, is most preferred. One face of the self-assembled monolayer is typically composed of chemical functionalities on the termini of the organic molecules that are chemisorbed or physisorbed onto the surface of the substrate or, if present, the coating on the substrate. Examples of suitable functionalities of monolayers include the positively charged amino groups of poly-L-lysine for use on negatively charged surfaces and thiols for use on gold surfaces. Typically, the other face of the self-assembled monolayer is exposed and may bear any number of chemical functionalities (end groups). Preferably, the molecules of the self-assembled monolayer are highly ordered.

A "self-assembled monolayer" is a monolayer which is created by the spontaneous assembly of molecules. The self-assembled monolayer may be ordered, disordered, or exhibit short- to long-range order.

An "affinity tag" is a functional moiety capable of directly or indirectly immobilizing a protein onto an exposed functionality of the organic thinfilm. Preferably, the affinity tag enables the site-specific immobilization and thus enhances orientation of the protein onto the organic thinfilm. In some cases, the affinity tag may be a simple chemical functional group. Other possibilities include amino acids, poly(amino acid) tags, or full-length proteins. Still other possibilities include carbohydrates and nucleic acids. For instance, the affinity tag may be a polynucleotide which hybridizes to another polynucleotide serving as a functional group on the organic thinfilm or another polynucleotide serving as an adaptor. The affinity tag may also be a synthetic chemical moiety. If the organic thinfilm of each of the patches comprises a lipid bilayer or monolayer, then a membrane anchor is a suitable affinity tag. The affinity tag may be covalently or noncovalently attached to the protein. For instance, if the affinity tag is covalently attached to the protein it may be attached via chemical conjugation or as a fusion protein. The affinity tag may also be attached to the protein via a cleavable linkage. Alternatively, the affinity tag may not be directly in contact with the protein. The affinity tag may instead be separated from the protein by an adaptor. The affinity tag may immobilize the protein to the organic thinfilm either through noncovalent interactions or through a covalent linkage.

An "adaptor", for purposes of this invention, is any entity that links an affinity tag to the immobilized protein of a patch of the array. The adaptor may be, but need not necessarily be, a discrete molecule that is noncovalently attached to both the affinity tag and the protein. The adaptor can instead be covalently attached to the affinity tag or the protein or both (via chemical conjugation or as a fusion protein, for instance). Proteins such as full-length proteins, polypeptides, or peptides are typical adaptors. Other possible adaptors include carbohydrates and nucleic acids.

The term "fusion protein" refers to a protein composed of two or more polypeptides that, although typically unjoined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological condition" means conditions that are typical inside a living organism or a cell. While it is recognized that some organs or organisms provide extreme conditions, the intra-organismal and intracellular environment normally varies around pH 7 (i.e., from pH 6.5 to pH 7.5), contains water as the predominant solvent, and exists at a temperature above 0° C. and below 50° C. It will be recognized that the concentration of various salts depends on the organ, organism, cell, or cellular compartment used as a reference.

"Proteomics" means the study of or the characterization of either the proteome or some fraction of the proteome. The "proteome" is the total collection of the intracellular proteins of a cell or population of cells and the proteins secreted by the cell or population of cells. This characterization most typically includes measurements of the presence, and usually quantity, of the proteins which have been expressed by a cell. The function, structural characteristics (such as post translational modification), and location within the cell of the proteins may also be studied. "Functional proteomics" refers to the study of the functional characteristics, activity level, and structural characteristics of the protein expression products of a cell or population of cells.

(b) Arrays of Proteins

The present invention is directed to arrays of proteins. Typically, the protein arrays comprise micrometer-scale, two-dimensional patterns of patches of proteins immobilized on an organic thinfilm coating on the surface of the substrate.

In one embodiment, the present invention provides an array of proteins which comprises a substrate, at least one organic thinfilm on some or all of the substrate surface, and a plurality of patches arranged in discrete, known regions on portions of the substrate surface covered by organic thinfilm, wherein each of said patches comprises a protein immobilized on the underlying organic thinfilm.

In most cases, the array will comprise at least about ten patches. In a preferred embodiment, the array comprises at least about 50 patches. In a particularly preferred embodiment the array comprises at least about 100 patches. In alternative preferred embodiments, the array of proteins may comprise more than $10^3$, $10^4$ or $10^5$ patches.

The area of surface of the substrate covered by each of the patches is preferably no more than about 0.25 $mm^2$. Preferably, the area of the substrate surface covered by each of the patches is between about 1 $\mu m^2$ and about 10,000 $\mu m^2$. In a particularly preferred embodiment, each patch covers an area of the substrate surface from about 100 $\mu m^2$ to about 2,500 $\mu m^2$. In an alternative embodiment, a patch on the array may cover an area of the substrate surface as small as about 2,500 $nm^2$, although patches of such small size are generally not necessary for the use of the array.

The patches of the array may be of any geometric shape. For instance, the patches may be rectangular or circular. The patches of the array may also be irregularly shaped.

The distance separating the patches of the array can vary. Preferably, the patches of the array are separated from neighboring patches by about 1 $\mu m$ to about 500 $\mu m$. Typically, the distance separating the patches is roughly proportional to the diameter or side length of the patches on the array if the patches have dimensions greater than about 10 $\mu m$. If the patch size is smaller, then the distance separating the patches will typically be larger than the dimensions of the patch.

In a preferred embodiment of the array, the patches of the array are all contained within an area of about 1 $cm^2$ or less on the surface of the substrate. In one preferred embodiment of the array, therefore, the array comprises 100 or more patches within a total area of about 1 $cm^2$ or less on the surface of the substrate. Alternatively, a particularly preferred array comprises $10^3$ or more patches within a total area of about 1 $cm^2$ or less. A preferred array may even optionally comprise $10^4$ or $10^5$ or more patches within an area of about 1 $cm^2$ or less on the surface of the substrate. In other embodiments of the invention, all of the patches of the array are contained within an area of about 1 $mm^2$ or less on the surface of the substrate.

Typically, only one type of protein is immobilized on each patch of the array. In a preferred embodiment of the array, the protein immobilized on one patch differs from the protein immobilized on a second patch of the same array. In such an embodiment, a plurality of different proteins are present on separate patches of the array. Typically the array comprises at least about ten different proteins. Preferably, the array comprises at least about 50 different proteins. More preferably, the array comprises at least about 100 different proteins. Alternative preferred arrays comprise more than about $10^3$ different proteins or more than about $10^4$ different proteins. The array may even optionally comprise more than about $10^5$ different proteins.

In one embodiment of the array, each of the patches of the array comprises a different protein. For instance, an array comprising about 100 patches could comprise about 100 different proteins. Likewise, an array of about 10,000 patches could comprise about 10,000 different proteins. In an alternative embodiment, however, each different protein is immobilized on more than one separate patch on the array. For instance, each different protein may optionally be present on two to six different patches. An array of the invention, therefore, may comprise about three-thousand protein patches, but only comprise about one thousand different proteins since each different protein is present on three different patches.

In another embodiment of the present invention, although the protein of one patch is different from that of another, the proteins are related. In a preferred embodiment, the two different proteins are members of the same protein family. The different proteins on the invention array may be either functionally related or just suspected of being functionally related. In another embodiment of the invention array, however, the function of the immobilized proteins may be unknown. In this case, the different proteins on the different patches of the array share a similarity in structure or sequence or are simply suspected of sharing a similarity in structure or sequence. Alternatively, the immobilized proteins may be just fragments of different members of a protein family.

The proteins immobilized on the array of the invention may be members of a protein family such as a receptor family (examples: growth factor receptors, catecholamine receptors, amino acid derivative receptors, cytokine receptors, lectins), ligand family (examples: cytokines, serpins), enzyme family (examples: proteases, kinases, phosphatases, ras-like GTPases, hydrolases), and transcription factors (examples: steroid hormone receptors, heat-shock transcription factors, zinc-finger proteins, leucine-zipper proteins, homeodomain proteins). In one embodiment, the different immobilized proteins are all HIV proteases or hepatitis C virus (HCV) proteases. In other embodiments of the invention, the immobilized proteins on the patches of the array are all hormone receptors, neurotransmitter receptors, extracellular matrix receptors, antibodies, DNA-binding proteins, intracellular signal transduction modulators and effectors, apoptosis-related factors, DNA synthesis factors, DNA repair factors, DNA recombination factors, or cell-surface antigens.

In a preferred embodiment, the protein immobilized on each patch is an antibody or antibody fragment. The antibodies or antibody fragments of the array may optionally be single-chain Fvs, Fab fragments, Fab' fragments, F(ab')$_2$ fragments, Fv fragments, dsFvs diabodies, Fd fragments, full-length, antigen-specific polyclonal antibodies, or full-length monoclonal antibodies. In a preferred embodiment, the immobilized proteins on the patches of the array are monoclonal antibodies, Fab fragments or single-chain Fvs.

In another preferred embodiment of the invention, the proteins immobilized to each patch of the array are protein-capture agents.

In an alternative embodiment of the invention array, the proteins on different patches are identical.

Biosensors, micromachined devices, and diagnostic devices that comprise the protein arrays of the invention are also contemplated by the present invention.

(c) Substrates, Coating, and Organic Thinfilms

The substrate of the array may be either organic or inorganic, biological or non-biological, or any combination of these materials. In one embodiment, the substrate is transparent or translucent. The portion of the surface of the substrate on which the patches reside is preferably flat and firm or semi-firm. However, the array of the present invention need not necessarily be flat or entirely two-dimensional. Significant topological features may be present on the surface of the substrate surrounding the patches, between the patches or beneath the patches. For instance, walls or other barriers may separate the patches of the array.

Numerous materials are suitable for use as a substrate in the array embodiment of the invention. For instance, the substrate of the invention array can comprise a material selected from a group consisting of silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for substrates of the array. In addition, many ceramics and polymers may also be used as substrates. Polymers which may be used as substrates include, but are not limited to, the following: polystyrene; poly(tetra)fluoroethylene (PTFE); polyvinylidenedifluoride; polycarbonate; polymethylmethacrylate; polyvinylethylene; polyethyleneimine; poly(etherether) ketone; polyoxymethylene (POM); polyvinylphenol; polylactides; polymethacrylimide (PMI); polyalkenesulfone (PAS); polypropylene; polyethylene; polyhydroxyethylmethacrylate (HEMA); polydimethylsiloxane; polyacrylamide; polyimide; and block-copolymers. Preferred substrates for the array include silicon, silica, glass, and polymers. The substrate on which the patches reside may also be a combination of any of the aforementioned substrate materials.

An array of the present invention may optionally further comprise a coating between the substrate and organic thinfilm on the array. This coating may either be formed on the substrate or applied to the substrate. The substrate can be modified with a coating by using thin-film technology based, for example, on physical vapor deposition (PVD), thermal processing, or plasma-enhanced chemical vapor deposition (PECVD). Alternatively, plasma exposure can be used to directly activate or alter the substrate and create a coating. For instance, plasma etch procedures can be used to oxidize a polymeric surface (i.e., polystyrene or polyethylene to expose polar functionalities such as hydroxyls, carboxylic acids, aldehydes and the like).

The coating is optionally a metal film. Possible metal films include aluminum, chromium, titanium, tantalum, nickel, stainless steel, zinc, lead, iron, copper, magnesium, manganese, cadmium, tungsten, cobalt, and alloys or oxides thereof. In a preferred embodiment, the metal film is a noble metal film. Noble metals that may be used for a coating include, but are not limited to, gold, platinum, silver, and copper. In an especially preferred embodiment, the coating comprises gold or a gold alloy. Electron-beam evaporation may be used to provide a thin coating of gold on the surface of the substrate. In a preferred embodiment, the metal film is from about 50 nm to about 500 nm in thickness. In an alternative embodiment, the metal film is from about 1 nm to about 1 $\mu$m in thickness.

In alternative embodiments, the coating comprises a composition selected from the group consisting of silicon, silicon oxide, titania, tantalum oxide, silicon nitride, silicon hydride, indium tin oxide, magnesium oxide, alumina, glass, hydroxylated surfaces, and polymers.

In one embodiment of the invention array, the surface of the coating is atomically flat. In this embodiment, the mean roughness of the surface of the coating is less than about 5 angstroms for areas of at least 25 $\mu m^2$. In a preferred embodiment, the mean roughness of the surface of the coating is less than about 3 angstroms for areas of at least 25 $\mu m^2$. The ultraflat coating can optionally be a template-stripped surface as described in Hegner et al., *Surface Science*, 1993, 291:39–46 and Wagner et al., *Langmuir*, 1995, 11:3867–3875, both of which are incorporated herein by reference.

It is contemplated that the coatings of many arrays will require the addition of at least one adhesion layer between said coating and the substrate. Typically, the adhesion layer will be at least 6 angstroms thick and may be much thicker. For instance, a layer of titanium or chromium may be desirable between a silicon wafer and a gold coating. In an alternative embodiment, an epoxy glue such as Epo-tek 377®, Epo-tek 301-2®, (Epoxy Technology Inc., Billerica, Mass.) may be preferred to aid adherence of the coating to the substrate. Determinations as to what material should be used for the adhesion layer would be obvious to one skilled in the art once materials are chosen for both the substrate and coating. In other embodiments, additional adhesion mediators or interlayers may be necessary to improve the optical properties of the array, for instance, in waveguides for detection purposes.

Deposition or formation of the coating (if present) on the substrate is performed prior to the formation of the organic thinfilm thereon. Several different types of coating may be combined on the surface. The coating may cover the whole surface of the substrate or only parts of it. The pattern of the coating may or may not be identical to the pattern of organic thinfilms used to immobilize the proteins. In one embodiment of the invention, the coating covers the substrate surface only at the site of the patches of the immobilized. Techniques useful for the formation of coated patches on the surface of the substrate which are organic thinfilm compatible are well known to those of ordinary skill in the art. For instance, the patches of coatings on the substrate may optionally be fabricated by photolithography, micromolding (PCT Publication WO 96/29629), wet chemical or dry etching, or any combination of these.

The organic thinfilm on which each of the patches of proteins is immobilized forms a layer either on the substrate itself or on a coating covering the substrate. The organic thinfilm on which the proteins of the patches are immobilized is preferably less than about 20 nm thick. In some embodiments of the invention, the organic thinfilm of each of the patches may be less than about 10 nm thick.

A variety of different organic thinfilms are suitable for use in the present invention. Methods for the formation of organic thinfilms include in situ growth from the surface, deposition by physisorption, spin-coating, chemisorption, self-assembly, or plasma-initiated polymerization from gas phase. For instance, a hydrogel composed of a material such as dextran can serve as a suitable organic thinfilm on the patches of the array. In one preferred embodiment of the invention, the organic thinfilm is a lipid bilayer. In another preferred embodiment, the organic thinfilm of each of the patches of the array is a monolayer. A monolayer of polyarginine or polylysine adsorbed on a negatively charged substrate or coating is one option for the organic thinfilm. Another option is a disordered monolayer of tethered polymer chains. In a particularly preferred embodiment, the organic thinfilm is a self-assembled monolayer. A monolayer of polylysine is one option for the organic thinfilm . The organic thinfilm is most preferably a self-assembled monolayer which comprises molecules of the formula X—R—Y, wherein R is a spacer, X is a functional group that binds R to the surface, and Y is a functional group for binding proteins onto the monolayer. In an alternative preferred embodiment, the self-assembled monolayer is comprised of molecules of the formula $(X)_a R(Y)_b$ where a and b are, independently, integers greater than or equal to 1 and X, R, and Y are as previously defined. In an alternative preferred embodiment, the organic thinfilm comprises a combination of organic thinfilms such as a combination of a lipid bilayer immobilized on top of a self-assembled monolayer of molecules of the formula X—R—Y. As another example, a monolayer of polylysine can also optionally be combined with a self-assembled monolayer of molecules of the formula X—R—Y (see U.S. Pat. No. 5,629,213).

In all cases, the coating, or the substrate itself if no coating is present, must be compatible with the chemical or physical adsorption of the organic thinfilm on its surface. For instance, if the patches comprise a coating between the substrate and a monolayer of molecules of the formula X—R—Y, then it is understood that the coating must be composed of a material for which a suitable functional group X is available. If no such coating is present, then it is understood that the substrate must be composed of a material for which a suitable functional group X is available.

In a preferred embodiment of the invention, the regions of the substrate surface, or coating surface, which separate the patches of proteins are free of organic thinfilm. In an alternative embodiment, the organic thinfilm extends beyond the area of the substrate surface, or coating surface if present, covered by the protein patches. For instance, optionally, the entire surface of the array may be covered by an organic thinfilm on which the plurality of spatially distinct patches of proteins reside. An organic thinfilm which covers the entire surface of the array may be homogenous or may optionally comprise patches of differing exposed functionalities useful in the immobilization of patches of different proteins. In still another alternative embodiment, the regions of the substrate surface, or coating surface if a coating is present, between the patches of proteins are covered by an organic thinfilm, but an organic thinfilm of a different type than that of the patches of proteins. For instance, the surfaces between the patches of proteins may be coated with an organic thinfilm characterized by low non-specific binding properties for proteins and other analytes.

A variety of techniques may be used to generate patches of organic thinfilm on the surface of the substrate or on the surface of a coating on the substrate. These techniques are well known to those skilled in the art and will vary depending upon the nature of the organic thinfilm, the substrate, and the coating if present. The techniques will also vary depending on the structure of the underlying substrate and the pattern of any coating present on the substrate. For instance, patches of a coating which is highly reactive with an organic thinfilm may have already been produced on the substrate surface. Arrays of patches of organic thinfilm can optionally be created by microfluidics printing, microstamping (U.S. Pat. Nos. 5,512,131 and 5,731,152), or microcontact printing ($\mu$CP) (PCT Publication WO 96/29629). Subsequent immobilization of proteins to the reactive monolayer patches results in two-dimensional arrays of the agents. Inkjet printer heads provide another option for patterning monolayer X—R—Y molecules, or components thereof, or other organic thinfilm components to nanometer or micrometer scale sites on the surface of the substrate or coating (Lemmo et al., Anal Chem., 1997, 69:543–551; U.S. Pat. Nos. 5,843, 767 and 5,837,860). In some cases, commercially available arrayers based on capillary dispensing (for instance, Omni-Grid™ from Genemachines, inc, San Carlos, Calif., and High-Throughput Microarrayer from Intelligent Bio-Instruments, Cambridge, Mass.) may also be of use in directing components of organic thinfilms to spatially distinct regions of the array.

Diffusion boundaries between the patches of proteins immobilized on organic thinfilms such as self-assembled monolayers may be integrated as topographic patterns (physical barriers) or surface functionalities with orthogonal wetting behavior (chemical barriers). For instance, walls of substrate material or photoresist may be used to separate some of the patches from some of the others or all of the patches from each other. Alternatively, non-bioreactive organic thinfilms, such as monolayers, with different wettability may be used to separate patches from one another.

In a preferred embodiment of the invention, each of the patches of proteins comprises a self-assembled monolayer of molecules of the formula X—R—Y, as previously defined, and the patches are separated from each other by surfaces free of the monolayer.

FIG. 1 shows the top view of one example of an array of 25 patches reactive with proteins. On the array, a number of patches 15 cover the surface of the substrate 3.

Figure 2:
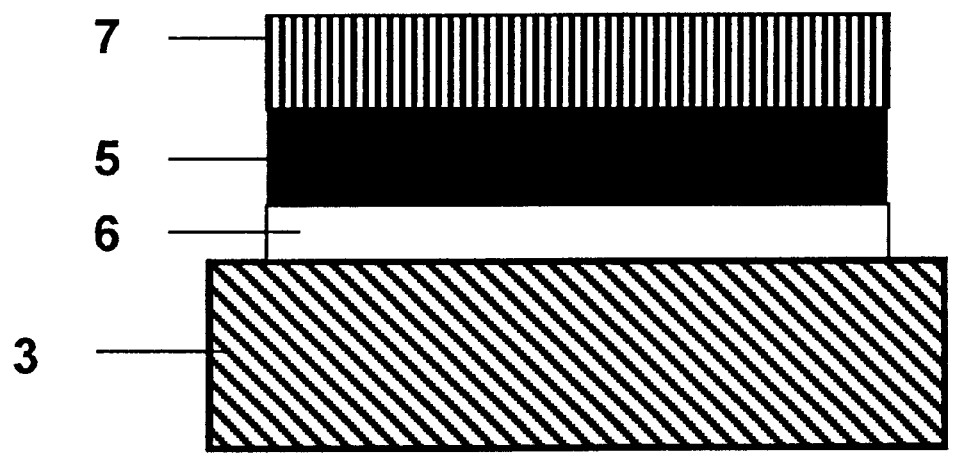
FIG. 2 shows the cross section of an individual patch of the array of FIG. 1.

FIG. 2 shows a detailed cross section of a patch 15 of the array of FIG. 1. This view illustrates the use of a coating 5 on the substrate 3. An adhesion interlayer 6 is also included in the patch. On top of the patch resides a self-assembled monolayer 7.

Figure 3:
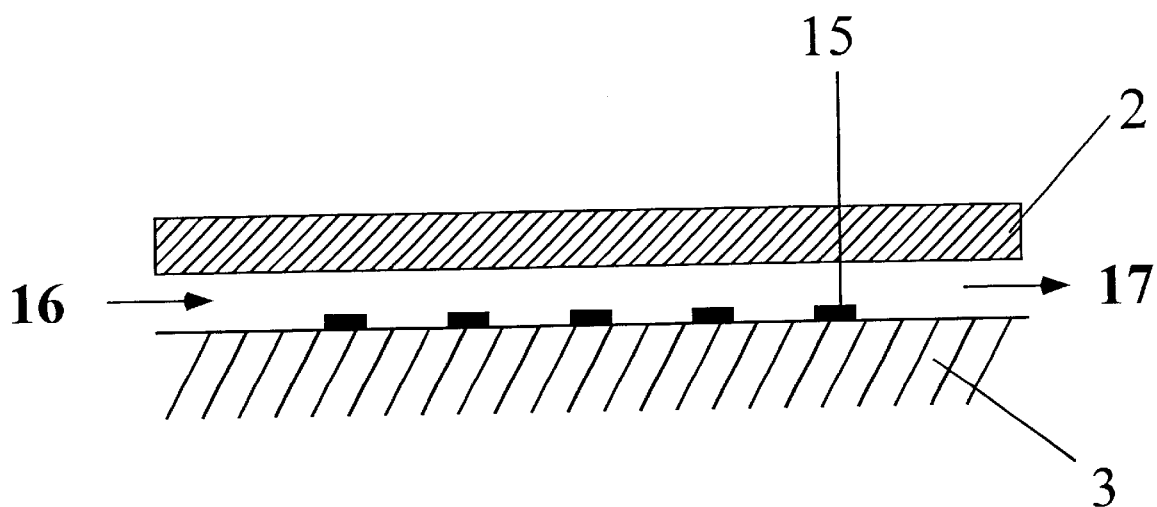
FIG. 3 shows the cross section of a row of monolayer-covered patches of the array of FIG. 1.

FIG. 3 shows a cross section of one row of the patches 15 of the array of FIG. 1. This figure also shows the use of a cover 2 over the array. Use of the cover 2 creates an inlet port 16 and an outlet port 17 for solutions to be passed over the array.

A variety of chemical moieties may function as monolayer molecules of the formula X—R—Y in the array of the present invention. However, three major classes of monolayer formation are preferably used to expose high densities of reactive omega-functionalities on the patches of the array: (i) alkylsiloxane monolayers ("silanes") on hydroxylated and non-hydroxylated surfaces (as taught in, for example, U.S. Pat. No. 5,405,766, PCT Publication WO 96/38726, U.S. Pat. Nos. 5,412,087, and 5,688,642); (ii) alkyl-thiol/dialkyldisulfide monolayers on noble metals (preferably Au(111) (as, for example, described in Allara et al., U.S. Pat. No. 4,690,715; Bamdad et al., U.S. Pat. No. 5,620,850; Wagner et al., Biophysical Journal, 1996, 70:2052–2066); and (iii) alkyl monolayer formation on oxide-free passivated silicon (as taught in, for example, Linford et al., J. Am. Chem. Soc., 1995, 117:3145–3155, Wagner et al., Journal of Structural Biology, 1997, 119:189–201, U.S. Pat. No. 5,429, 708). One of ordinary skill in the art, however, will recognize that many possible moieties may be substituted for X R, and/or Y, dependent primarily upon the choice of substrate, coating, and affinity tag. Many examples of monolayers are described in Ulman, An Introduction to Ultrathin Organic Films: From Langmuir-Blodgett to Self Assembly, Academic press (1991).

In one embodiment, the monolayer comprises molecules of the formula $(X)_aR(Y)_b$ wherein a and b are, independently, equal to an integer between 1 and about 200. In a preferred embodiment, a and b are, independently, equal to an integer between 1 and about 80. In a more preferred embodiment, a and b are, independently, equal to 1 or 2. In a most preferred embodiment, a and b are both equal to 1 (molecules of the formula X—R—Y).

If the patches of the invention array comprise a self-assembled monolayer of molecules of the formula $(X)_aR(Y)_b$, then R may optionally comprise a linear or branched hydrocarbon chain from about 1 to about 400 carbons long. The hydrocarbon chain may comprise an alkyl, aryl, alkenyl, alknyl, cycloalkyl, alkaryl, aralkyl group, or any combination thereof. If a and b are both equal to one, then R is typically an alkyl chain from about 3 to about 30 carbons long. In a preferred embodiment, if a and b are both equal to one, then R is an alkyl chain from about 8 to about 22 carbons long and is, optionally, a straight alkane. However, it is also contemplated that in an alternative embodiment, R may readily comprise a linear or branched hydrocarbon chain from about 2 to about 400 carbons long and be interrupted by at least one hetero atom. The interrupting hetero groups can include —O—, —CONH—, —CONHCO—, —NH—, —CSNH—, —CO—, —CS—, —S—, —SO—, —(OCH$_2$CH$_2$)$_n$— (where n=1–20), —(CF$_2$)$_n$— (where n=1–22), and the like. Alternatively, one or more of the hydrogen moieties of R can be substituted with deuterium. In alternative, less preferred, embodiments, R may be more than about 400 carbons long.

X may be chosen as any group which affords chemisorption or physisorption of the monolayer onto the surface of the substrate (or the coating, if present). When the substrate or coating is a metal or metal alloy, X, at least prior to incorporation into the monolayer, can in one embodiment be chosen to be an asymmetrical or symmetrical disulfide, sulfide, diselenide, selenide, thiol, isonitrile, selenol, a trivalent phosphorus compound, isothiocyanate, isocyanate, xanthanate, thiocarbamate, a phosphine, an amine, thio acid or a dithio acid. This embodiment is especially preferred when a coating or substrate is used that is a noble metal such as gold, silver, or platinum.

If the substrate of the array is a material such as silicon, silicon oxide, indium tin oxide, magnesium oxide, alumina, quartz, glass, or silica, then the array of one embodiment of the invention comprises an X that, prior to incorporation into said monolayer, is a monohalosilane, dihalosilane, trihalosilane, trialkoxysilane, dialkoxysilane, or a monoalkoxysilane. Among these silanes, trichlorosilane and trialkoxysilane are particularly preferred.

In a preferred embodiment of the invention, the substrate is selected from the group consisting of silicon, silicon dioxide, indium tin oxide, alumina, glass, and titania; and X, prior to incorporation into said monolayer, is selected from the group consisting of a monohalosilane, dihalosilane, trihalosilane, trichlorosilane, trialkoxysilane, dialkoxysilane, monoalkoxysilane, carboxylic acids, and phosphates.

In another preferred embodiment of the invention, the substrate of the array is silicon and X is an olefin.

In still another preferred embodiment of the invention, the coating (or the substrate if no coating is present) is titania or tantalum oxide and X is a phosphate.

In other embodiments, the surface of the substrate (or coating thereon) is composed of a material such as titanium oxide, tantalum oxide, indium tin oxide, magnesium oxide, or alumina where X is a carboxylic acid or phosphoric acid. Alternatively, if the surface of the substrate (or coating thereon) of the array is copper, then X may optionally be a hydroxamic acid.

If the substrate used in the invention is a polymer, then in many cases a coating on the substrate such as a copper coating will be included in the array. An appropriate functional group X for the coating would then be chosen for use in the array. In an alternative embodiment comprising a polymer substrate, the surface of the polymer may be plasma-modified to expose desirable surface functionalities for monolayer formation. For instance, EP 780423 describes the use of a monolayer molecule that has an alkene X functionality on a plasma exposed surface. Still another possibility for the invention array comprised of a polymer is that the surface of the polymer on which the monolayer is formed is functionalized by copolymerization of appropriately functionalized precursor molecules.

Another possibility is that prior to incorporation into the monolayer, X can be a free-radical-producing moiety. This functional group is especially appropriate when the surface on which the monolayer is formed is a hydrogenated silicon surface. Possible free-radical producing moieties include, but are not limited to, diacylperoxides, peroxides, and azo compounds. Alternatively, unsaturated moieties such as unsubstituted alkenes, alkynes, cyano compounds and isonitrile compounds can be used for X, if the reaction with X is accompanied by ultraviolet, infrared, visible, or microwave radiation.

In alternative embodiments, X, prior to incorporation into the monolayer, may be a hydroxyl, carboxyl, vinyl, sulfonyl, phosphoryl, silicon hydride, or an amino group.

The component, Y, of the monolayer is a functional group responsible for binding a protein onto the monolayer. In a preferred embodiment of the invention, the Y group is either highly reactive (activated) towards the protein or is easily converted into such an activated form. In a preferred embodiment, the coupling of Y with the protein occurs readily under normal physiological conditions not detrimental to the activity of the protein. The functional group Y may either form a covalent linkage or a noncovalent linkage with the protein (or its affinity tag, if present). In a preferred embodiment, the functional group Y forms a covalent linkage with the protein or its affinity tag. It is understood that following the attachment of the protein (with or without an affinity tag) to Y, the chemical nature of Y may have changed. Upon attachment of the protein, Y may even have been removed from the organic thinfilm.

In one embodiment of the array of the present invention, Y is a functional group that is activated in situ. Possibilities for this type of functional group include, but are not limited to, such simple moieties such as a hydroxyl, carboxyl, amino, aldehyde, carbonyl, methyl, methylene, alkene, alkyne, carbonate, aryliodide, or a vinyl group. Appropriate modes of activation would be obvious to one skilled in the art. Alternatively, Y can comprise a functional group that requires photoactivation prior to becoming activated enough to trap the protein.

In an especially preferred embodiment of the array of the present invention, Y is a complex and highly reactive functional moiety that is compatible with monolayer formation and needs no in situ activation prior to reaction with the protein and/or affinity tag. Such possibilities for Y include, but are not limited to, maleimide, N-hydroxysuccinimide (Wagner et al., *Biophysical Journal*, 1996, 70:2052–2066), nitrilotriacetic acid (U.S. Pat. No. 5,620,850), activated hydroxyl, haloacetyl, bromoacetyl, iodoacetyl, activated carboxyl, hydrazide, epoxy, aziridine, sulfonylchloride, trifluoromethyldiaziridine, pyridyldisulfide, N-acylimidazole, imidazolecarbamate, vinylsulfone, succinimidylcarbonate, arylazide, anhydride, diazoacetate, benzophenone, isothiocyanate, isocyanate, imidoester, fluorobenzene, and biotin.

Figure 4:
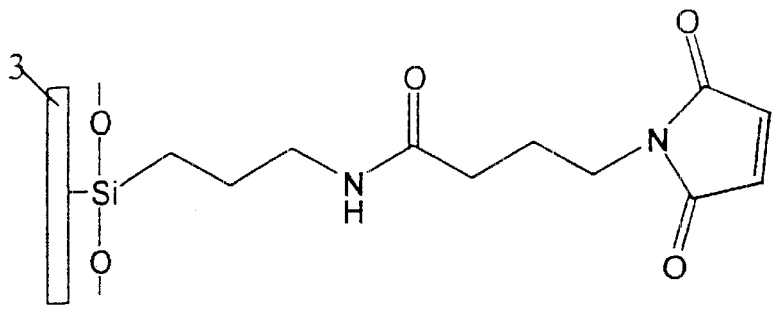
FIG. 4 shows a thiolreactive monolayer on a substrate.

FIG. 4 shows one example of a monolayer on a substrate 3. In this example, substrate 3 comprises glass. The monolayer is thiolreactive because it bears a maleimidyl functional group Y.

Figure 5:
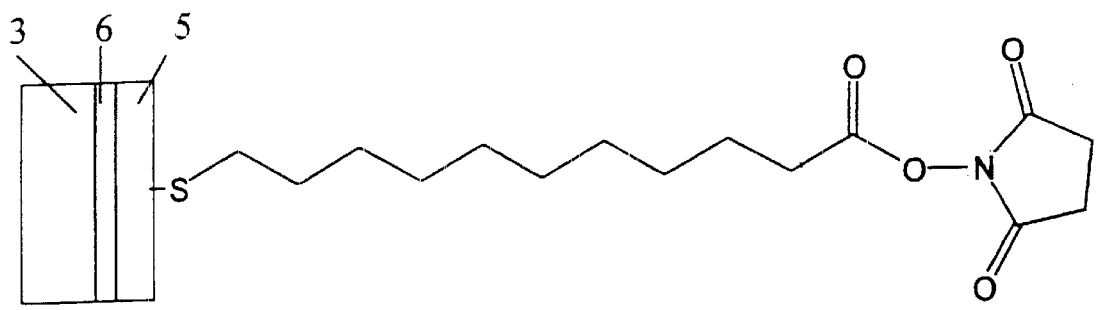
FIG. 5 shows an aminoreactive monolayer on a coated substrate.

FIG. 5 shows another example of a monolayer on a substrate 3 which is silicon. In this case, however, a thinfilm gold coating 5 covers the surface of the substrate 3. Also, in this embodiment, a titanium adhesion interlayer 6 is used to adhere the coating 5 to the substrate 3. This monolayer is aminoreactive because it bears an N-hydroxysuccinimidyl functional group Y.

In an alternative embodiment, the functional group Y of the array is selected from the group of simple functional moieties. Possible Y functional groups include, but are not limited to, —OH, —$NH_2$, —COOH, —COOR, —RSR, —$PO_4^{-3}$, —$OSO_3^{-2}$, —$SO_3^-$, —$COO^-$, —$SOO^-$, —$CONR_2$, —CN, —$NR_2$, and the like.

The monolayer molecules of the present invention can optionally be assembled on the surface in parts. In other words, the monolayer need not necessarily be constructed by chemisorption or physisorption of molecules of the formula X—R—Y to the surface of the substrate (or coating). Instead, in one embodiment, X may be chemisorbed or physisorbed to the surface of the substrate (or coating) alone first. Then, R or even just individual components of R can be attached to X through a suitable chemical reaction. Upon completion of addition of the spacer R to the X moiety already immobilized on the surface, Y can be attached to the ends of the monolayer molecule through a suitable covalent linkage.

Not all self-assembled monolayer molecules on a given patch need be identical to one another. Some patches may comprise mixed monolayers. For instance, the monolayer of an individual patch may optionally comprise at least two different molecules of the formula X—R—Y, as previously described. This second X—R—Y molecule may optionally immobilize the same protein as the first. In addition, some of the monolayer molecules X—R—Y of a patch may have failed to attach any protein.

As another alternative embodiment of the invention, a mixed, self-assembled monolayer of an individual patch on the array may comprise both molecules of the formula X—R—Y, as previously described, and molecules of the formula, X—R—V where R is a spacer, X is a functional group that binds R to the surface, and V is a moiety which is biocompatible with proteins and resistant to the non-specific binding of proteins. For example, V may consist of a hydroxyl, saccharide, or oligo/polyethylene glycol moiety (EP Publication 780423).

In still another embodiment of the invention, the array comprises at least one unreactive patch of organic thinfilm on the substrate or coating surface which is devoid of any protein. For instance, the unreactive patch may optionally comprise a monolayer of molecules of the formula X—R—V, where R is a spacer, X is a functional group that binds R to the surface, and V is a moiety resistant to the non-specific binding of proteins. The unreactive patch may serve as a control patch or be useful in background binding measurements.

Regardless of the nature of the monolayer molecules, in some arrays it may be desirable to provide crosslinking between molecules of an individual patch's monolayer. In general, crosslinking confers additional stability to the monolayer. Such methods are familiar to those skilled in the art (for instance, see Ulman, *An Introduction to Ultrathin Organic Films: From Langmuir-Blodgett to Self-Assembly*, Academic Press (1991)).

After completion of formation of the monolayer on the patches, the protein may be attached to the monolayer via interaction with the Y-functional group. Y-functional groups which fail to react with any proteins are preferably quenched prior to use of the array.

(d) Affinity Tags and Immobilization of the Proteins

In a preferred embodiment, the protein-immobilizing patches of the array further comprise an affinity tag that enhances immobilization of the protein onto the organic thinfilm. The use of an affinity tag on the protein of the array typically provides several advantages. An affinity tag can confer enhanced binding or reaction of the protein with the functionalities on the organic thinfilm, such as Y if the organic thinfilm is a an X—R—Y monolayer as previously described. This enhancement effect may be either kinetic or thermodynamic. The affinity tag/thinfilm combination used in the patches of the array preferably allows for immobilization of the proteins in a manner which does not require harsh reaction conditions that are adverse to protein stability or function. In most embodiments, immobilization to the organic thinfilm in aqueous, biological buffers is ideal.

An affinity tag also preferably offers immobilization on the organic thinfilm that is specific to a designated site or location on the protein (site-specific immobilization). For this to occur, attachment of the affinity tag to the protein must be site-specific. Site-specific immobilization helps ensure that the active site or binding site of the immobilized protein, such as the antigen-binding site of the antibody moiety, remains accessible to ligands in solution. Another advantage of immobilization through affinity tags is that it allows for a common immobilization strategy to be used with multiple, different proteins.

The affinity tag is optionally attached directly, either covalently or noncovalently, to the protein. In an alternative embodiment, however, the affinity tag is either covalently or noncovalently attached to an adaptor which is either covalently or noncovalently attached to the protein.

In a preferred embodiment, the affinity tag comprises at least one amino acid. The affinity tag may be a polypeptide comprising at least two amino acids which is reactive with the functionalities of the organic thinfilm. Alternatively, the affinity tag may be a single amino acid which is reactive with the organic thinfilm. Examples of possible amino acids which could be reactive with an organic thinfilm include cysteine, lysine, histidine, arginine, tyrosine, aspartic acid, glutamic acid, tryptophan, serine, threonine, and glutamine. A polypeptide or amino acid affinity tag is preferably expressed as a fusion protein with the immobilized protein of each patch. Amino acid affinity tags provide either a single amino acid or a series of amino acids that can interact with the functionality of the organic thinfilm, such as the Y-functional group of the self-assembled monolayer molecules. Amino acid affinity tags can be readily introduced into recombinant proteins to facilitate oriented immobilization by covalent binding to the Y-functional group of a monolayer or to a functional group on an alternative organic thinfilm.

The affinity tag may optionally comprise a poly(amino acid) tag. A poly(amino acid) tag is a polypeptide that comprises from about 2 to about 100 residues of a single amino acid, optionally interrupted by residues of other amino acids. For instance, the affinity tag may comprise a poly-cysteine, polylysine, poly-arginine, or poly-histidine. Amino acid tags are preferably composed of two to twenty residues of a single amino acid, such as, for example, histidines, lysines, arginines, cysteines, glutamines, tyrosines, or any combination of these. According to a preferred embodiment, an amino acid tag of one to twenty amino acids includes at least one to ten cysteines for thioether linkage; or one to ten lysines for amide linkage; or one to ten arginines for coupling to vicinal dicarbonyl groups. One of ordinary skill in the art can readily pair suitable affinity tags with a given functionality on an organic thinfilm.

The position of the amino acid tag can be at an amino-, or carboxy-terminus of the protein of a patch of the array, or anywhere in-between, as long as the active site or binding site of the protein remains in a position accessible for ligand interaction. Where compatible with the protein chosen, affinity tags introduced for protein purification are preferentially located at the C-terminus of the recombinant protein to ensure that only full-length proteins are isolated during protein purification. For instance, if intact antibodies are used on the arrays, then the attachment point of the affinity tag on the antibody is preferably located at a C-terminus of the effector (Fc) region of the antibody. If scFvs are used on the arrays, then the attachment point of the affinity tag is also preferably located at the C-terminus of the molecules.

Affinity tags may also contain one or more unnatural amino acids. Unnatural amino acids can be introduced using suppressor tRNAs that recognize stop codons (i.e., amber) (Noren et al., *Science,* 1989, 244:182–188; Ellman et al., *Methods Enzym.,* 1991, 202:301–336; Cload et al., *Chem. Biol.,* 1996, 3:1033–1038). The tRNAs are chemically amino-acylated to contain chemically altered ("unnatural") amino acids for use with specific coupling chemistries (i.e., ketone modifications, photoreactive groups).

In an alternative embodiment the affinity tag can comprise an intact protein, such as, but not limited to, glutathione S-transferase, an antibody, avidin, or streptavidin.

Other protein conjugation and immobilization techniques known in the art may be adapted for the purpose of attaching affinity tags to the protein. For instance, in an alternative embodiment of the array, the affinity tag may be an organic bioconjugate which is chemically coupled to the protein of interest. Biotin or antigens may be chemically cross linked to the protein. Alternatively, a chemical crosslinker may be used that attaches a simple functional moiety such as a thiol or an amine to the surface of a protein to be immobilized on a patch on the array. Alternatively, protein synthesis or protein ligation techniques known to those skilled in the art may be used to attach an affinity tag to a protein. For instance, intein-mediated protein ligation may optionally be used to attach the affinity tag to the protein (Mathys, et al., *Gene* 231:1–13, 1999; Evans, et al., *Protein Science* 7:2256–2264, 1998).

In an alternative embodiment of the invention, the organic thinfilm of each of the patches comprises, at least in part, a lipid monolayer or bilayer, and the affinity tag comprises a membrane anchor. Optionally, the lipid monolayer or bilayer is immobilized on a self-assembled monolayer.

Figure 6:
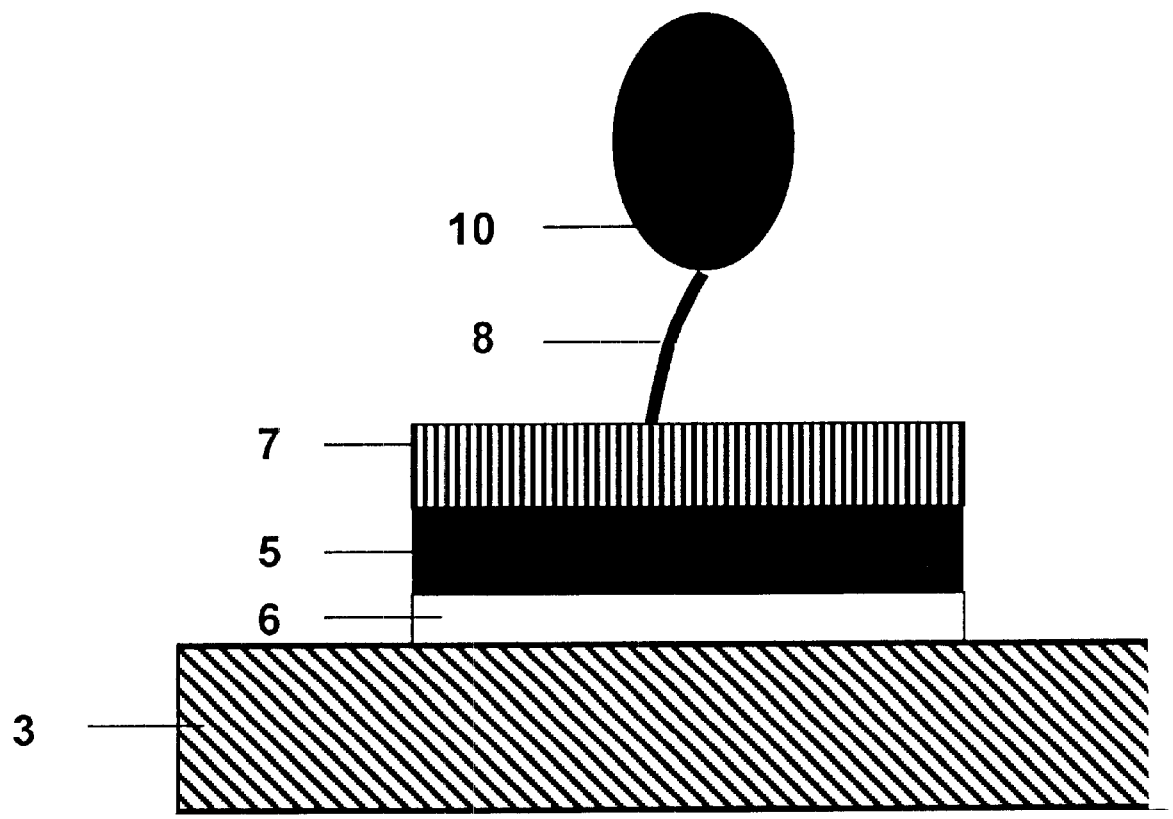
FIG. 6 shows the immobilization of a protein on a monolayer-coated substrate via an affinity tag.

FIG. 6 shows a detailed cross section of a patch on one embodiment of the invention array. In this embodiment, a protein 10 is immobilized on a monolayer 7 on a substrate 3. An affinity tag 8 connects the protein 10 to the monolayer 7. The monolayer 7 is formed on a coating 5 which is separated from the substrate 3 by an interlayer 6.

In an alternative embodiment of the invention, no affinity tag is used to immobilize the proteins onto the organic thinfilm. An amino acid or other moiety (such as a carbohydrate moiety) inherent to the protein itself may instead be used to tether the protein to the reactive group of the organic thinfilm. In preferred embodiments, the immobilization is site-specific with respect to the location of the site of immobilization on the protein. For instance, the sulfhydryl group on the C-terminal region of the heavy chain portion of a Fab' fragment generated by pepsin digestion of an antibody, followed by selective reduction of the disulfide between monovalent Fab' fragments, may be used as the affinity tag. Alternatively, a carbohydrate moiety on the Fc portion of an intact antibody can be oxidized under mild conditions to an aldehyde group suitable for immobilizing the antibody on a monolayer via reaction with a hydrazide-activated Y group on the monolayer. Examples of immobilization of proteins without any affinity tag can be found in Wagner et al., *Biophys. J.,* 70:2437–2441, 1996 and the specific examples, Examples 8–10, below.

When the proteins of at least some of the different patches on the array are different from each other, different solutions, each containing a different, preferably, affinity-tagged protein, must be delivered to their individual patches. Solutions of proteins may be transferred to the appropriate patches via arrayers which are well-known in the art and even commercially available. For instance, microcapillary-based dispensing systems may be used. These dispensing systems are preferably automated and computer-aided. A description of and building instructions for an example of a microarrayer comprising an automated capillary system can be found on the internet at http://cmgm.stanford.edu/pbrown/array.html and http://cmgm.stanford.edu/pbrown/mguide/index.html. The use of other microprinting techniques for transferring solutions containing the proteins to the protein-reactive patches is also possible. Ink-jet printer heads may also optionally be used for precise delivery of the proteins to the protein-reactive patches. Representative, non-limiting disclosures of techniques useful for depositing the proteins on the patches may be found, for example, in U.S. Pat. Nos. 5,731,152 (stamping apparatus), U.S. Pat. No. 5,807,522 (capillary dispensing device), U.S. Pat. No. 5,837,860 (ink-jet printing technique, Hamilton 2200 robotic pipetting delivery system), and U.S. Pat. No. 5,843,767 (ink-jet printing technique, Hamilton 2200 robotic pipetting delivery system), all incorporated by reference herein.

(e) Adaptors

Another embodiment of the arrays of the present invention comprises an adaptor that links the affinity tag to the immobilized protein. The additional spacing of the protein from the surface of the substrate (or coating) that is afforded by the use of an adaptor is particularly advantageous since proteins are known to be prone to surface inactivation. The adaptor may optionally afford some additional advantages as well. For instance, the adaptor may help facilitate the attachment of the protein to the affinity tag. In another embodiment, the adaptor may help facilitate the use of a particular detection technique with the array. One of ordinary skill in the art will be able to choose an adaptor which is appropriate for a given affinity tag. For instance, if the affinity tag is streptavidin, then the adaptor could be a biotin molecule that is chemically conjugated to the protein which is to be immobilized.

In a preferred embodiment, the adaptor is a protein. In a preferred embodiment, the affinity tag, adaptor, and protein to be immobilized together compose a fusion protein. Such a fusion protein may be readily expressed using standard recombinant DNA technology. Adaptors which are proteins are especially useful to increase the solubility of the protein of interest and to increase the distance between the surface of the substrate or coating and the protein of interest. Use of an adaptor which is a protein can also be very useful in facilitating the preparative steps of protein purification by affinity binding prior to immobilization on the array. Examples of possible adaptors which are proteins include glutathione-S-transferase (GST), maltose-binding protein, chitin-binding protein, thioredoxin, green-fluorescent protein (GFP). GFP can also be used for quantification of surface binding. If the protein immobilized on the patches of the array is an antibody or antibody fragment comprising an Fc region, then the adaptor may optionally be protein G, protein A, or recombinant protein A/G (a gene fusion product secreted from a non-pathogenic form of Bacillus which contains four Fc binding domains from protein A and two from protein G).

Figure 7:
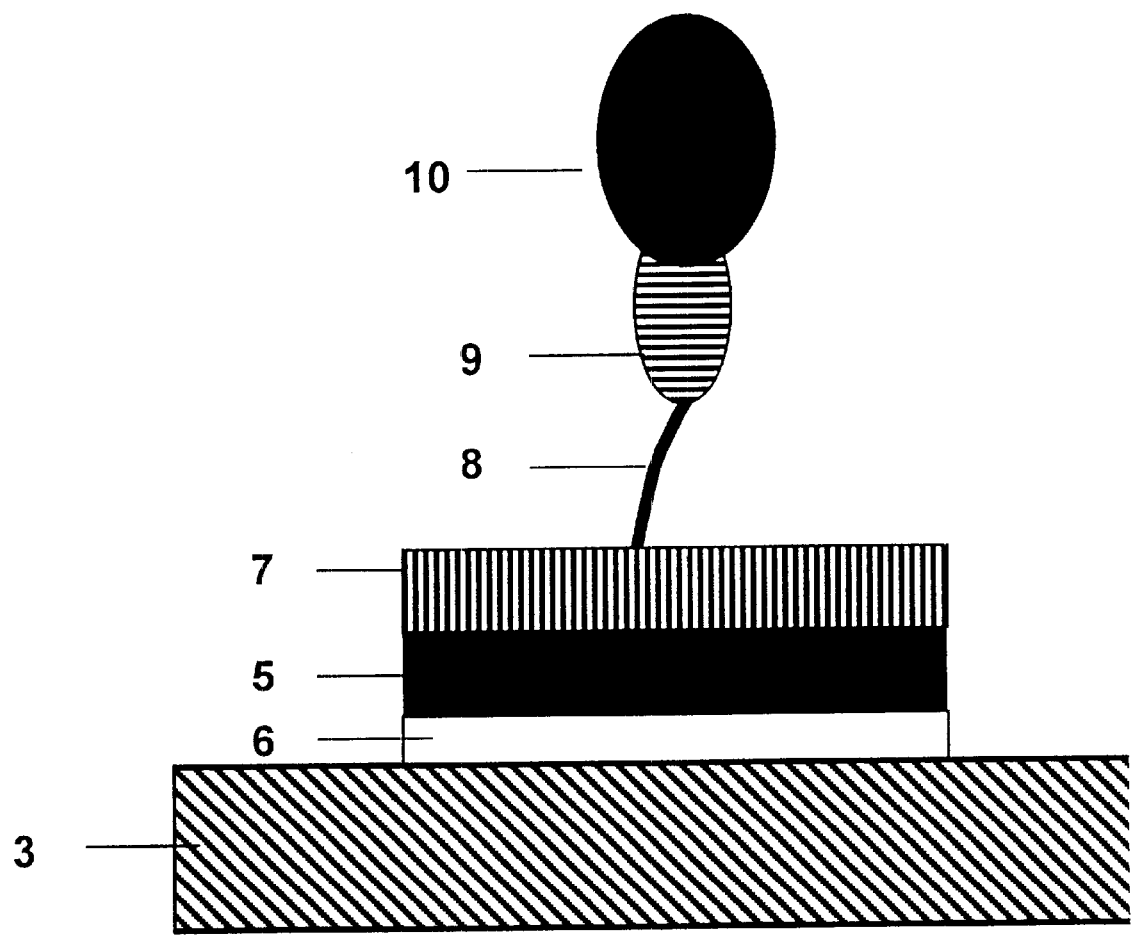
FIG. 7 shows the immobilization of a protein on a monolayer-coated substrate via an affinity tag and an adaptor.

FIG. 7 shows a cross section of a patch on one particular embodiment of the invention array. The patch comprises a protein 10 immobilized on a monolayer 7 via both an affinity tag 8 and an adaptor molecule 9. The monolayer 7 rests on a coating 5. An interlayer 6 is used between the coating 5 and the substrate 3.

(f) Preparation of the Proteins of the Array

The proteins immobilized on the array may be produced by any of the variety of means known to those of ordinary skill in the art.

In preparation for immobilization to the arrays of the present invention, the protein can optionally be expressed from recombinant DNA either in vivo or in vitro. The cDNA of the protein to be immobilized on the array is cloned into an expression vector (many examples of which are commercially available) and introduced into cells of the appropriate organism for expression. A broad range of host cells and expression systems may be used to produce the proteins to be immobilized on the array. For in vivo expression of the proteins, cDNAs can be cloned into commercial expression vectors (Qiagen, Novagen, Clontech, for example) and introduced into an appropriate organism for expression. Expression in vivo may be done in bacteria (for example, *Escherichia coli*), plants (for example, *Nicotiana tabacum*), lower eukaryotes (for example, *Saccharomyces cerevisiae, Saccharomyces pombe, Pichia pastoris*), or higher eukaryotes (for example, bacculovirus-infected insect cells, insect cells, mammalian cells). For in vitro expression PCR-amplified DNA sequences are directly used in coupled in vitro transcription/translation systems (for instance: *Escherichia coli* S30 lysates from T7 RNA polymerase expressing, preferably protease-deficient strains; wheat germ lysates; reticulocyte lysates (Promega, Pharmacia, Panvera)). The choice of organism for optimal expression depends on the extent of post-translational modifications (i.e., glycosylation, lipid-modifications) desired. One of ordinary skill in the art will be able to readily choose which host cell type is most suitable for the protein to be immobilized and application desired.

DNA sequences encoding amino acid affinity tags and adaptor protein sequences are engineered into the expression vectors such that the genes of interest can be cloned in frame either 5' or 3' of the DNA sequence encoding the affinity tag and adaptor.

The expressed proteins are purified by affinity chromatography using commercially available resins.

Preferably, production of families of related proteins involves parallel processing from cloning to protein expression and protein purification. cDNAs for the protein of interest will be amplified by PCR using cDNA libraries or EST (expressed sequence tag) clones as templates. Any of the in vitro or in vivo expression systems described above can then be used for expression of the proteins to be immobilized on the array.

*Escherichia coli*-based protein expression is generally the method of choice for soluble proteins that do not require extensive post-translational modifications for activity. Extracellular or intracellular domains of membrane proteins will be fused to protein adaptors for expression and purification.

The entire approach can be performed using 96-well assay plates. PCR reactions are carried out under standard conditions. Oligonucleotide primers contain unique restriction sites for facile cloning into the expression vectors. Alternatively, the TA cloning system (Clontech) can be used. Expression vectors contain the sequences for affinity tags and the protein adaptors. PCR products are ligated into the expression vectors (under inducible promoters) and introduced into the appropriate competent *Escherichia coli* strain by calcium-dependent transformation (strains include: XL-1 blue, BL21, SG13009(lon-)). Transformed *Escherichia coli* cells are plated and individual colonies transferred into 96-array blocks. Cultures are grown to mid-log phase, induced for expression, and cells collected by centrifugation. Cells are resuspended containing lysozyme and the membranes broken by rapid freeze/thaw cycles, or by sonication. Cell debris is removed by centrifugation and the supernatants transferred to 96-tube arrays. The appropriate affinity matrix is added, protein of interest bound and nonspecifically bound proteins removed by repeated washing steps using 12–96 pin suction devices and centrifugation. Alternatively, magnetic affinity beads and filtration devices can be used (Qiagen). The proteins are eluted and transferred to a new 96-well array. Protein concentrations are determined and an aliquot of each protein is spotted onto a nitrocellulose filter and verified by Western analysis using an antibody directed against the affinity tag. The purity of each sample is assessed by SDS-PAGE and silver staining or mass spectrometry. Proteins are snap-frozen and stored at −80° C.

*Saccharomyces cerevisiae* allows for core glycosylation and lipid modifications of proteins. The approach described above for *Escherichia coli* can be used with slight modifications for transformation and cell lysis. Transformation of *Saccharomyces cerevisiae* is by lithium-acetate and cell lysis is either by lyticase digestion of the cell walls followed by freeze-thaw, sonication or glass-bead extraction. Variations of post-translational modifications can be obtained by different yeast strains (i.e. *Saccharomyces pombe, Pichia pastoris*).

The advantage of the bacculovirus system or mammalian cells are the wealth of post-translational modifications that can be obtained. The bacculo-system requires cloning of viruses, obtaining high titer stocks and infection of liquid insect cell suspensions (cells are SF9, SF21). Mammalian cell-based expression requires transfection and cloning of cell lines. Soluble proteins are collected from the medium while intracellular or membrane bound proteins require cell lysis (either detergent solubilization, freeze-thaw). Proteins can then be purified analogous to the procedure described for *Escherichia coli*.

For in vitro translation the system of choice is *Escherichia coli* lysates obtained from protease-deficient and T7 RNA polymerase overexpressing strains. *Escherichia coli* lysates provide efficient protein expression (30–50 µg/ml lysate). The entire process is carried out in 96-well arrays. Genes of interest are amplified by PCR using oligonucleotides that contain the gene-specific sequences containing a T7 RNA polymerase promoter and binding site and a sequence encoding the affinity tag. Alternatively, an adaptor protein can be fused to the gene of interest by PCR. Amplified DNAs can be directly transcribed and translated in the *Escherichia coli* lysates without prior cloning for fast analysis. The proteins are then isolated by binding to an affinity matrix and processed as described above.

Alternative systems which may be used include wheat germ extracts and reticulocyte extracts. In vitro synthesis of membrane proteins and or post-translationally modified proteins will require reticulocyte lysates in combination with microsomes.

In one preferred embodiment of the invention, the proteins immobilized on the patches of the array are antibodies. Optionally, the immobilized proteins may be monoclonal antibodies. The production of monoclonal antibodies against specific protein targets is routine using standard hybridoma technology. In fact, numerous monoclonal antibodies are available commercially.

As an alternative to obtaining antibodies or antibody fragments which have been produced by cell fusion or from continuous cell lines, the antibody moieties may be expressed in bacteriophage. Such antibody phage display technologies are well known to those skilled in the art. The bacteriophage expression systems allow for the random recombination of heavy- and light-chain sequences, thereby creating a library of antibody sequences which can be selected against the desired antigen. The expression system can be based on bacteriophage λ or, more preferably, on filamentous phage. The bacteriophage expression system can be used to express Fab fragments, Fv's with an engineered intermolecular disulfide bond to stabilize the $V_H$–$V_L$ pair (dsFv's), scFvs, or diabody fragments.

The antibody genes of the phage display libraries may be from pre-immunized donors. For instance, the phage display library could be a display library prepared from the spleens of mice previously immunized with a mixture of proteins (such as a lysate of human T-cells). Immunization can optionally be used to bias the library to contain a greater number of recombinant antibodies reactive towards a specific set of proteins (such as proteins found in human T-cells). Alternatively, the library antibodies may be derived from naive or synthetic libraries. The naive libraries have been constructed from spleens of mice which have not been contacted by external antigen. In a synthetic library, portions of the antibody sequence, typically those regions corresponding to the complementarity determining regions (CDR) loops, have been mutagenized or randomized.

The phage display method involves batch-cloning the antibody gene library into a phage genome as a fusion to the gene encoding one of the phage coat proteins (pIII, pVI, or pVIII). The pIII phage protein gene is preferred. When the fusion product is expressed it is incorporated into the mature phage coat. As a result, the antibody is displayed as a fusion on the surface of the phage and is available for binding and hence, selection, on a target protein. Once a phage particle is selected as bearing an antibody-coat protein fusion with the desired affinity towards the target protein, the genetic material within the phage particle which corresponds to the displayed antibody can be amplified and sequenced or otherwise analyzed.

In a preferred embodiment, a phagemid is used as the expression vector in the phage display procedures. A phagemid is a small plasmid vector that carries gene III with appropriate cloning sites and a phage packaging signal and contains both host and phage origins of replication. The phagemid is unable to produce a complete phage as the gene III fusion is the only phage gene encoded on the phagemid. A viable phage can be produced by infecting cells containing the phagemid with a helper phage containing a defective replication origin. A hybrid phage emerges which contains all of the helper phage proteins as well as the gene III-rAb fusion. The emergent phage contains the phagemid DNA only.

In a preferred embodiment of the invention, the recombinant antibodies used in phage display methods of preparing antibody fragments for the arrays of the invention are expressed as genetic fusions to the bacteriophage gene III protein on a phagemid vector. For instance, the antibody variable regions encoding a single-chain Fv fragment can be fused to the amino terminus of the gene III protein on a phagemid. Alternatively, the antibody fragment sequence could be fused to the amino terminus of a truncated pIII sequence lacking the first two N-terminal domains. The phagemid DNA encoding the antibody-pIII fusion is preferably packaged into phage particles using a helper phage such as M13KO7 or VCS-M13, which supplies all structural phage proteins.

To display Fab fragments on phage, either the light or heavy (Fd) chain is fused via its C-terminus to pIII. The partner chain is expressed without any fusion to pIII so that both chains can associate to form an intact Fab fragment.

Any method of selection may be used which separates those phage particles which do bind the target protein from those which do not. The selection method must also allow for the recovery of the selected phages. Most typically, the phage particles are selected on an immobilized target protein. Some phage selection strategies known to those skilled in the art include the following: panning on an immobilized antigen; panning on an immobilized antigen using specific elution; using biotinylated antigen and then selecting on a streptavidin resin or streptavidin-coated magnetic beads; affinity purification; selection on Western blots (especially useful for unknown antigens or antigens difficult to purify); in vivo selection; and pathfinder selection. If the selected phage particles are amplified between selection rounds, multiple iterative rounds of selection may optionally be performed.

Elution techniques will vary depending upon the selection process chosen, but typical elution techniques include washing with one of the following solutions: HCl or glycine buffers; basic solutions such as triethylamine; chaotropic agents; solutions of increased ionic strength; or DTT when biotin is linked to the antigen by a disulfide bridge. Other typical methods of elution include enzymatically cleaving a protease site engineered between the antibody and gene III, or by competing for binding with excess antigen or excess antibodies to the antigen.

A method for producing an array of antibody fragments therefore comprises first selecting recombinant bacteriophage which express antibody fragments from a phage display library. The recombinant bacteriophage are selected by affinity binding to the desired antigen. (Iterative rounds of selection are possible, but optional.) Next, at least one purified sample of an antibody fragment from a bacteriophage which was selected in the first step is produced. This antibody production step typically entails infecting *E. coli* cells with the selected bacteriophage. In the absence of helper phage, the selected bacteriophage then replicate as expressive plasmids without producing phage progeny. Alternatively, the antibody fragment gene of the selected recombinant bacteriophage is isolated, amplified, and then expressed in a suitable expression system. In either case, following amplification, the expressed antibody fragment of the selected and amplified recombinant bacteriophage is isolated and purified. In a third step of the method, the earlier steps of phage display selection and purified antibody fragment production are repeated using affinity binding to antigens from before until the desired plurality of purified samples of different antibody fragments with different binding partners are produced. In a final step of the method, the antibody fragment of each different purified sample is immobilized onto organic thinfilm on a separate patch on the surface of a substrate to form a plurality of patches of antibody fragments on discrete, known regions of the substrate surface covered by organic thinfilm.

For instance, to generate an antibody array with antibody fragments against known antigens, open reading frames of the known protein targets identified in DNA databases are amplified by polymerase chain reaction and transcribed and translated in vitro to produce proteins on which a recombinant bacteriophage expressing single-chain antibody fragments are selected. Once selected, the antibody fragment sequence of the selected bacteriophage is amplified (typically using the polymerase chain method) and recloned into a desirable expression system. The expressed antibody fragments are purified and then printed onto organic thinfilms on substrates to form the high density arrays.

In the preparation of the arrays of the invention, phage display methods analogous to those used for antibody fragments may be used for other proteins which are to be immobilized on an array of the invention as long as the protein is of suitable size to be incorporated into the phagemid or alternative vector and expressed as a fusion with a bacteriophage coat protein. Phage display techniques using non-antibody libraries typically make use of some type of protein host scaffold structure which supports the variable regions. For instance, β-sheet proteins, α-helical handle proteins, and other highly constrained protein structures have been used as host scaffolds.

Alternative display vectors may also be used to produce the proteins which are printed on the arrays of the invention. Polysomes, stable protein-ribosome-mRNA complexes, can be used to replace live bacteriophage as the display vehicle for recombinant antibody fragments or other proteins (Hanes and Pluckthun, *Proc. Natl. Acad. Sci USA*, 94:4937–4942, 1997). The polysomes are formed by preventing release of newly synthesized and correctly folded protein from the ribosome. Selection of the polysome library is based on binding of the antibody fragments or other proteins which are displayed on the polysomes to the target protein. mRNA which encodes the displayed protein or antibody having the desired affinity for the target is then isolated. Larger libraries may be used with polysome display than with phage display.

(g) Uses of the Arrays

The present invention also provides for methods of using the invention array. The arrays of the present invention are particularly suited for the use in drug development. Other uses include medical diagnostics, proteomics and biosensors.

Use of one of the protein arrays of the present invention may optionally involve placing the two-dimensional protein array in a flowchamber with approximately 1–10 microliters of fluid volume per 25 $mm^2$ overall surface area. The cover over the array in the flowchamber is preferably transparent or translucent. In one embodiment, the cover may comprise Pyrex or quartz glass. In other embodiments, the cover may be part of a detection system that monitors interaction between biological moieties immobilized on the array and an analyte. The flowchambers should remain filled with appropriate aqueous solutions to preserve protein activity. Salt, temperature, and other conditions are preferably kept similar to those of normal physiological conditions. Analytes and potential drug compounds may be flushed into the flow chamber as desired and their interaction with the immobilized proteins determined. Sufficient time must be given to allow for binding between the immobilized proteins and an analyte to occur. No specialized microfluidic pumps, valves, or mixing techniques are required for fluid delivery to the array.

Alternatively, fluid can be delivered to each of the patches of the array individually. For instance, in one embodiment, the regions of the substrate surface may be microfabricated in such a way as to allow integration of the array with a number of fluid delivery channels oriented perpendicular to the array surface, each one of the delivery channels terminating at the site of an individual protein-coated patch.

The sample which is delivered to the array is typically a fluid.

In general, delivery of solutions containing proteins to be bound by the proteins of the array may optionally be preceded, followed, or accompanied by delivery of a blocking solution. A blocking solution contains protein or another moiety which will adhere to sites of non-specific binding on the array. For instance, solutions of bovine serum albumin or milk may be used as blocking solutions.

A wide range of detection methods is applicable to the methods of the invention. As desired, detection may be either quantitative or qualitative. The invention array can be interfaced with optical detection methods such as absorption in the visible or infrared range, chemoluminescence, and fluorescence (including lifetime, polarization, fluorescence correlation spectroscopy (FCS), and fluorescence-resonance energy transfer (FRET)). Furthermore, other modes of detection such as those based on optical waveguides (PCT Publication WO 96/26432 and U.S. Pat. No. 5,677,196), surface plasmon resonance, surface charge sensors, and surface force sensors are compatible with many embodiments of the invention. Alternatively, technologies such as those based on Brewster angle microscopy (Schaaf et al., *Langmuir*, 3:1131–1135 (1987)) and ellipsometry (U.S. Pat. Nos. 5,141,311 and 5,116,121; Kim, *Macromolecules*, 22:2682–2685 (1984)) can be used in conjunction with the arrays of the invention. Quartz crystal microbalances and desorption processes (see for example, U.S. Pat. No. 5,719,060) provide still other alternative detection means suitable for at least some embodiments of the invention array. An example of an optical biosensor system compatible both with some arrays of the present invention and a variety of non-label detection principles including surface plasmon resonance, total internal reflection fluorescence (TIRF), Brewster Angle microscopy, optical waveguide lightmode spectroscopy (OWLS), surface charge measurements, and ellipsometry can be found in U.S. Pat. No. 5,313,264.

Although non-label detection methods are generally preferred, some of the types of detection methods commonly used for traditional immunoassays which require the use of labels may be applied to use with at least some of the arrays of the present invention, especially those arrays which are arrays of protein-capture agents. These techniques include noncompetitive immunoassays, competitive immunoassays, and dual label, ratiometric immunoassays. These particular techniques are primarily suitable for use with the arrays of proteins when the number of different proteins with different specificity is small (less than about 100). In the competitive method, binding-site occupancy is determined indirectly. In this method, the proteins of the array are exposed to a labeled developing agent, which is typically a labeled version of the analyte or an analyte analog. The developing agent competes for the binding sites on the protein with the analyte. The fractional occupancy of the proteins on different patches can be determined by the binding of the developing agent to the proteins of the individual patches. In the noncompetitive method, binding site occupancy is determined directly. In this method, the patches of the array are exposed to a labeled developing agent capable of binding to either the bound analyte or the occupied binding sites on the protein. For instance, the developing agent may be a labeled antibody directed against occupied sites (i.e., a "sandwich assay"). Alternatively, a dual label, ratiometric, approach may be taken where the immobilized protein is labeled with one label and the second, developing agent is labeled with a second label (Ekins, et al., *Clinica Chimica Acta.,* 194:91–114, 1990). Many different labeling methods may be used in the aforementioned techniques, including radioisotopic, enzymatic, chemiluminescent, and fluorescent methods. Fluorescent methods are preferred.

Figure 8:
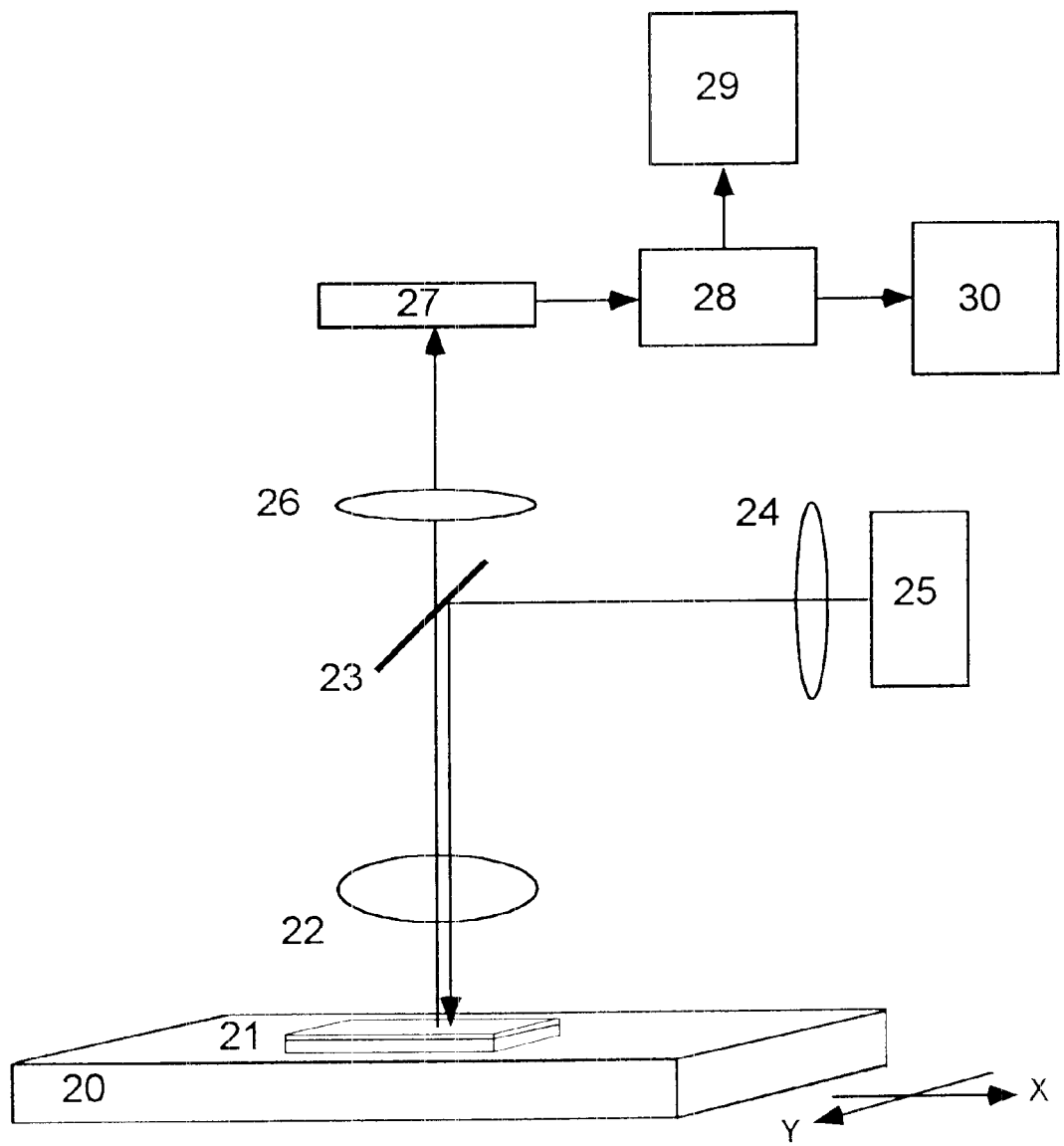
FIG. 8 shows a schematic of a fluorescence detection unit which may be used to monitor interaction of the proteins of the array with an analyte.

FIG. 8 shows a schematic diagram of one type of fluorescence detection unit which may be used to monitor interaction of immobilized proteins of an array with an analyte. In the illustrated detection unit, the protein array 21 is positioned on a base plate 20. Light from a 100 W mercury arc lamp 25 is directed through an excitation filter 24 and onto a beam splitter 23. The light is then directed through a lens 22, such as a Micro Nikkor 55 mm 1:2:8 lens, and onto the array 21. Fluorescence emission from the array returns through the lens 22 and the beam splitter 23. After next passing through an emission filter 26, the emission is received by a cooled CCD camera 27, such as the Slowscan TE/CCD-1024SF&SB (Princeton Instruments). The camera is operably connected to a CPU 28 which is in turn operably connected to a VCR 29 and a monitor 30.

Figure 9:
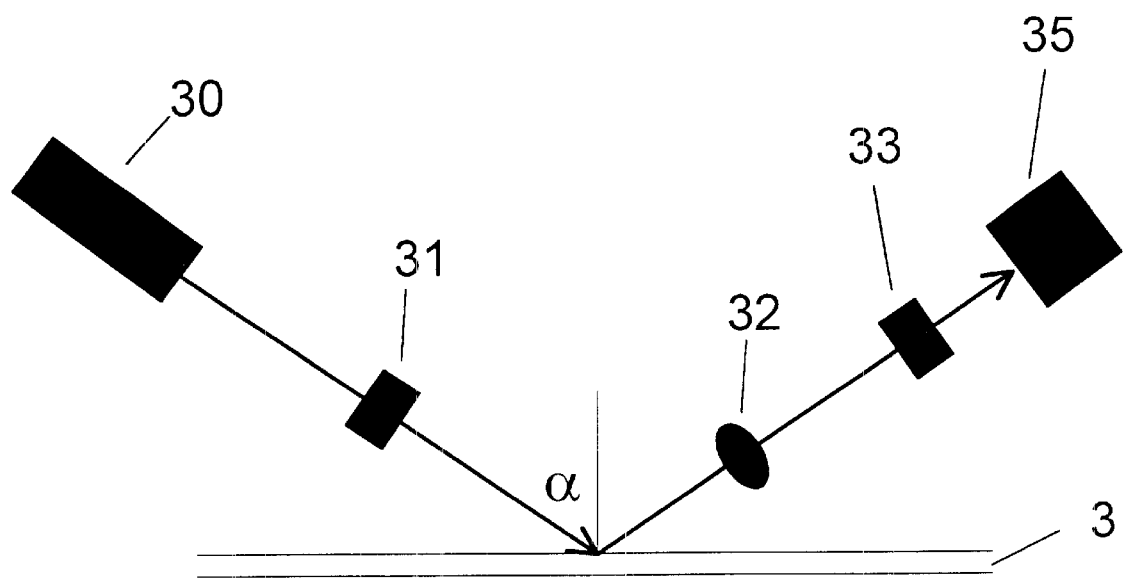
FIG. 9 shows a schematic of an ellipsometric detection unit which may be used to monitor interactions between analytes and the proteins of the array.

FIG. 9 shows a schematic diagram of an alternative detection method based on ellipsometry. Ellipsometry allows for information about the sample to be determined from the observed change in the polarization state of a reflected light wave. Interaction of an analyte with a layer of immobilized proteins on a patch results in a thickness change and alters the polarization status of a plane-polarized light beam reflected off the surface. This process can be monitored in situ from aqueous phase and, if desired, in imaging mode. In a typical setup, monochromatic light (e.g. from a He—Ne laser, 30) is plane polarized (polarizer 31) and directed onto the surface of the sample and detected by a detector 35. A compensator 32 changes the elliptically polarized reflected beam to plane-polarized. The corresponding angle is determined by an analyzer 33 and then translated into the ellipsometric parameters Psi and Delta which change upon binding of analyte with the immobilized proteins. Additional information can be found in Azzam, et al., *Ellipsometry and Polarized Light*, North-Holland Publishing Company: Amsterdam, 1977.

In one embodiment, the invention provides a method for screening a plurality of proteins for their ability to interact with a component of a sample comprising the steps of delivering the sample to a protein array of the invention comprising the proteins to be screened and detecting for the interaction of the component with the immobilized protein of each patch. Optionally, the component may be a protein.

Possible interactions towards which the present invention may be directed include, but are not limited to, antibody/antigen, antibody/hapten, enzyme/substrate, carrier protein/substrate, lectin/carbohydrate, receptor/hormone, receptor/effector, protein/DNA, protein/RNA, repressor/inducer, or the like. The interaction may involve binding and/or catalysis. The array of he invention is even suitable for assaying translocation by a membrane through a lipid bilayer. In preferred embodiments of use of the array, the assayed interaction is a binding interaction. The assayed interaction may be between a potential drug candidate and a plurality of potential drug targets. For instance, a synthesized organic compound may be tested for its ability to act as an inhibitor to a family of immobilized receptors.

Another aspect of the invention provides for a method for screening a plurality of proteins for their ability to bind a particular component of a sample. This method comprises delivering the sample to a protein array of the invention comprising the proteins to be screened and detecting, either directly or indirectly, for the presence or amount of the particular component retained at each patch. In a preferred embodiment, the method further comprises the intermediate step of washing the array to remove any unbound or non-specifically bound components of the sample from the array before the detection step. In another embodiment, the method further comprises the additional step of further characterizing the particular component retained on at least one patch. The particular component may optionally be a protein.

The optional step of further characterizing the particular component retained on a patch of the array is typically designed to identify the nature of the component bound to the protein of a particular patch. In some cases, the entire identity of the component may not be known and the purpose of the further characterization may be the initial identification of the mass, sequence, structure and/or activity (if any) of the bound component. In other cases, the basic identity of the component may be known, but some information about the component may not be known. For instance it may be known that the component is a particular protein, but the post-translational modification, activation state, or some other feature of the protein may not be known. In one embodiment, the step of further characterizing components which are proteins involves measuring the activity of the proteins. Although in some cases it may be preferable to remove the component from the patch before the step of further characterizing the protein is carried out, in other cases the component can be further characterized while still bound to the patch. In still further embodiments, the proteins of the patch which binds a component can be used to isolate and/or purity the component on a larger scale, such as by purifying a component which is a protein from cells. The purified sample of the component can then be characterized through traditional means such as microsequencing, mass spectrometry, and the like.

In another embodiment of the invention, a method of assaying for protein-protein binding interactions is provided which comprises the following steps: first, delivering a sample comprising at least one protein to be assayed for binding to the protein array of the invention; and then detecting, either directly, or indirectly, for the presence or amount of the protein from the sample which is retained at each patch. In a preferred embodiment, the method further comprises an additional step prior to the detection step which comprises washing the array to remove unbound or nonspecifically bound components of the sample from the array. Typically, the protein being assayed for binding will be from the same organism as the proteins immobilized on the array.

Another embodiment of the invention provides a method of assaying in parallel for the presence of a plurality of analytes in a sample which can react with one or more of the immobilized proteins on the protein array. This method comprises delivering the sample to the invention array and detecting for the interaction of the analyte with the immobilized protein at each patch.

In still another embodiment of the invention, a method of assaying in parallel for the presence of a plurality of analytes in a sample which can bind one or more of the immobilized proteins on the protein array comprises delivering the fluid sample to the invention array and detecting, either directly or indirectly, for the presence or amount of analyte retained at each patch. In a preferred embodiment, the method further comprises the step of washing the array tot remove any unbound or non-specifically bound components of the sample from the array.

The array may be used in a diagnostic manner when the plurality of analytes being assayed are indicative of a disease condition or the presence of a pathogen in an organism. In such embodiments, the sample which is delivered to the array will then typically be derived from a body fluid or a cellular extract from the organism.

The array may be used for drug screening when a potential drug candidate is screened directly for its ability to bind or otherwise interact with a plurality of proteins on the invention array. Alternatively, a plurality of potential drug candidates may be screened in parallel for their ability to bind or otherwise interact with one or more immobilized proteins on the array. The drug screening process may optionally involve assaying for the interaction, such as binding, of at least one analyte or component of a sample with one or more immobilized proteins on an invention array, both in the presence and absence of the potential drug candidate. This allows for the potential drug candidate to be tested for its ability to act as an inhibitor of the interaction or interactions originally being assayed.

(h) EXAMPLES

The following specific examples are intended to illustrate the invention and should not be construed as limiting the scope of the claims:

Example 1

Fabrication of a Two-dimensional Array by Photolithography

In a preferred embodiment of the invention, two-dimensional arrays are fabricated onto the substrate material via standard photolithography and/or thin film deposition. Alternative techniques include microcontact printing. Usually, a computer-aided design pattern is transferred to a photomask using standard techniques, which is then used to transfer the pattern onto a silicon wafer coated with photoresist.

In a typical example, the array ("chip") with lateral dimensions of 10×10 mm comprises squared patches of a bioreactive layer (here: gold as the coating on a silicon substrate) each 0.1×0.1 mm in size and separated by hydrophobic surface areas with a 0.2 mm spacing. 4" diameter Si(100) wafers (Virginia Semiconductor) are used as bulk materials. Si(100) wafers are first cleaned in a 3:1 mixture of $H_2SO_4$, conc.: 30% $H_2O_2$ (90° C., 10 min), rinsed with deionized water (18 MΩcm), finally passivated in 1% aqueous HF, and singed at 150° C. for 30 min to become hydrophobic. The wafer is then spincoated with photoresist (Shipley 1813), prebaked for 25 minutes at 90° C., exposed using a Karl Suss contact printer and developed according to standard protocols. The wafer is then dried and postbaked at 110° C. for 25 min. In the next step, the wafer is primed with a titanium layer of 20 nm thickness, followed by a 200 nm thick gold layer. Both layers were deposited using electron-beam evaporation (5 Å/s). After resist stripping and a short plasma treatment, the gold patches can be further chemically modified to achieve the desired bioreactive and biocompatible properties (see Example 3, below).

Example 2

Fabrication of a Two-dimensional Array by Deposition Through a Hole Mask

In another preferred embodiment the array of gold patches is fabricated by thin film deposition through a hole mask which is in direct contact with the substrate. In a typical example, Si(100) wafers are first cleaned in a 3:1 mixture of $H_2SO_4$, conc.: 30% $H_2O_2$ (90° C., 10 min), rinsed with deionized water (18 MΩcm), finally passivated in 1% aqueous HF and singed at 150° C. for 30 min to become hydrophobic. The wafer is then brought into contact with a hole mask exhibiting the positive pattern of the desired patch array. In the next step, the wafer is primed with a titanium layer of 20 nm thickness, followed by a 200 nm thick gold layer. Both layers were deposited using electron-beam evaporation (5 Å/s). After removal of the mask, the gold patches can be further chemically modified to achieve the desired bioreactive and biocompatible properties (see Example 3, below).

Example 3

Synthesis of an Aminoreactive Monolayer Molecule (Following the Procedure Outlined in Wagner et al., *Biophys. J.*, 1996, 70:2052–2066)

General. $^1$H- and $^{13}$C-NMR spectra are recorded on Bruker instruments (100 to 400 MHz). Chemical shifts (δ) are reported in ppm relative to internal standard (($CH_3)_4Si$, δ=0.00 ($^1$H- and $^{13}$C-NMR)). FAB-mass spectra are recorded on a VG-SABSEQ instrument ($Cs^+$, 20 keV). Transmission infrared spectra are obtained as dispersions in KBr on an FTIR Perkin-Elmer 1600 Series instrument. Thin-layer chromatography (TLC) is performed on pre-coated silica gel 60 F254 plates (MERCK, Darmstadt, FRG), and detection was done using $Cl_2$/toluidine, $PdCl_2$ and UV-detection under NH3-vapor. Medium pressure liquid chromatography (MPLC) is performed on a Labomatic MD-80 (LABOMATIC INSTR. AG, Allschwil, Switzerland) using a Buechi column (460×36 mm; BUECHI, Flawil, Switzerland), filled with silica gel 60 (particle size 15–40 μm) from Merck.

Synthesis of 11,11'-dithiobis(succinimidylundecanoate) (DSU). Sodium thiosulfate (55.3 g, 350 mmol) is added to a suspension of 11-bromo-undecanoic acid (92.8 g, 350 mmol) in 50% aqueous 1,4-dioxane (1000 ml). The mixture is heated at reflux (90° C.) for 2 h until the reaction to the intermediate Bunte salt was complete (clear solution). The oxidation to the corresponding disulfide is carried out in situ by adding iodine in portions until the solution retained with a yellow to brown colour. The surplus of iodine is retitrated with 15% sodium pyrosulfite in water. After removal of 1,4-dioxane by rotary evaporation the creamy suspension is filtered to yield product 11,11'-dithiobis(undecanoic acid). Recrystallization from ethyl acetate/THF provides a white solid (73.4 g, 96.5%): mp 94° C.; $^1$H NMR (400 MHz, CDCl$_3$/CD$_3$OD 95: 5): δ2.69 (t, 2H, J=7.3 Hz), 2.29 (t, 2H, J=7.5 Hz), 1.76–1.57 (m, 4H), and 1.40–1.29 (m, 12H); FAB-MS (Cs$^+$, 20 keV): m/z (relative intensity) 434 (100, M$^+$). Anal. Calcd. for C$_{22}$H$_{42}$O$_4$S$_2$: C, 60.79; H, 9.74; S, 14.75. Found: C, 60.95; H, 9.82; S, 14.74. To a solution of 11,11'-dithiobis(undecanoic acid). (1.0 g, 2.3 mmol) in THF (50 ml) is added N-hydroxysuccinimide (0.575 g, 5 mmol) followed by DCC (1.03 g, 5 mmol) at 0° C. After the reaction mixture is allowed to warm to 23° C. and is stirred for 36 h at room temperature, the dicyclohexylurea (DCU) is filtered. Removal of the solvent under reduced pressure and recrystallization from acetone/hexane provides 11,11'-dithiobis(succinimidylundecanoate) as a white solid. Final purification is achieved by medium pressure liquid chromatography (9 bar) using silica gel and a 2:1 mixture of ethyl acetate and hexane. The organic phase is concentrated and dried in vacuum to afford 11,11'-dithiobis (succinimidylundecanoate) (1.12 g, 78%): mp 95° C.; $^1$H NMR (400 MHz, CDCl$_3$): δ2.83 (s, 4H), 2.68 (t, 2H, J=7.3 Hz), 2.60 (t, 2H, J=7.5 Hz), 1.78–1.63 (m, 4H), and 1.43–1.29 (m, 12H); FAB-MS (Cs$^+$, 20 keV): m/z (relative intensity) 514 (100), 628 (86, M$^+$). Anal. Calcd. for C$_{30}$H$_{48}$N$_2$O$_8$S$_2$: C, 57.30; H, 7.69; N, 4.45; S, 10.20. Found: C, 57.32; H, 7.60; N, 4.39; S, 10.25.

Example 4

Formation of an Aminoreactive Monolayer on Gold (Following the Procedure of Wagner et al., Biophys. J., 1996, 70:2052–2066).

Monolayers based on 11,11'-dithiobis (succinimidylundecanoate) (DSU) can be deposited on Au(111) surfaces of microarrays described under Examples 1 and 2 by immersing them into a 1 mM solution of DSU in chloroform at room temperature for 1 hour. After rinsing with 10 volumes of solvent, the N-hydroxysuccinimidyl-terminated monolayer is dried under a stream of nitrogen and immediately used for protein immobilization.

Example 5

Expression and Purification of Human Caspase Fusion Proteins

Caspases are cysteine proteases of the papain superfamily, with a different active site and catalytic mechanism than observed for papain, Wilson, K. P. et al., Nature, 1994 370:270–275. Caspases are important enzymes in the promotion of the cell death pathways and inflammation, Villa, et al., TIBS, 1997, 22:288–392. Identification of selective caspase inhibitors is essential to prevent cross-inhibition of other caspase-dependent pathways. Caspases 1, 2, 3, 4, 5, 6, 7, 8, 9, 10, Villa, et al., TIBS, 1997, 22:288–392 and new caspase homologs identified by the human genome project are PCR amplified and cloned into an E. coli expression vector containing an N-terminal histidine tag, Hochuli, et al., Biotechnology, 1988 6:1321, a factor Xa cleavage site, a lysine tag and a tri-glycine linker. Fusion proteins are expressed, purified by nickel-nitrilotriacetic acid (NTA) agarose chromatography, the histidine tag removed by factor Xa cleavage, followed by gel filtration. Caspases are snap-frozen and stored in 20 mM PIPES, pH 7.2, 150 mM NaCl, 0.1% CHAPS, 10% sucrose at –80° C.

Example 6

Immobilization of Fusion Proteins on a 2D-protein Array

Caspase-fusion proteins can be immobilized to the aminoreactive monolayer surface of the bioreactive patches of the two-dimensional array (see Examples 1, 2, and 4 above). Caspase fusion proteins can be diluted to concentrations of 1 μg/ml in 20 mM PIPES, pH 7.2, 150 mM NaCl, 0.1% CHAPS, 10% sucrose and applied onto the bioreactive patches using a computer-aided, capillary-based dispensing system. After an immobilization period of 30 min, the 2D array was rinsed and subjected to analysis. Ultrapure water with a resistance of 18 MΩcm is generally useable for all aqueous buffers (purified by passage through a Barnstead Nanopure® system).

Example 7

Assay of Caspase Activity on a Two-dimensional Array

Caspase activity can be determined by a binding assay using three fluorescently labeled peptide aldehyde inhibitors that form a reversible thiohemiacetal moiety with the active site cysteine, Thornberry, Methods in Enzymology, 1994, 244:615–631. The peptides are adapted to caspase 1, 3, 4, 7: Dns (dansyl)-SS-DEVD-CHO, caspase 1: Dns-SS-VDVAD-CHO, caspase 6: Dns-SS-VQID-CHO, Talanian, J. Biol. Chem., 1997, 272:9677–9682. The affinity for Ac-DEVD-CHO to caspase 1 is determined to be in the low nanomolar range, Thornberry, Methods in Enzymology, 1994, 244:615–631. The assay buffer is 20 mM PIPES, pH 7.2, 150 mM NaCl, 0.1% CHAPS, 10% sucrose, Stennicke, and Salvesen, J. Biol. Chem., 1997, 272:25719–25723. Fluorescently labeled peptides are mixed to a final concentration of 1 to 5 nM each, the potential drug compound added and flushed onto the 2D array. Peptides are allowed to bind for 10–60 min., unbound peptide removed by washing with buffer and the fluorescence intensity measured (excitation at 360 nm, emission at 470 nm).

Example 8

Formation and Use of an Array of Immobilized Fab' Antibody Fragments to Detect Concentrations of Soluble Proteins Prepared From Cultured Mammalian Cells Collections of IgG antibodies are purchased from commercial sources (e.g. Pierce, Rockford, Ill.). The antibodies are first purified by affinity chromatography based on binding to immobilized protein A. The antibodies are diluted 1:1 in binding buffer( 0.1 M Tris-HCl, 0.15 M NaCl, pH 7.5). A 2 ml minicolumn containing a gel with immobilized protein A is prepared. (Hermanson, et. al., Immobilized Affinity Ligand Techniques, Academic Press, San Diego, 1992.) The column is equilibrated with 10 ml of binding buffer. Less than 10 mg of immunoglobulin is applied to each 2 ml minicolumn and the column is washed with binding buffer until the absorbance at 280 nm is less than 0.02. The bound immunoglobulins are eluted with 0.1 M glycine, 0.15 M NaCl, pH 2.8, and immediately neutralized with 1.0 M Tris-HCl, pH 8.0 to 50 mM final concentration and then dialyzed against 10 mM sodium phosphate, 0.15 M NaCl, pH 7.2 and stored at 4° C.

The purified immunoglobulin are digested with immobilized pepsin. Pepsin is an acidic endopeptidase and hydrolyzes proteins favorably adjacent to aromatic and dicarboxylic L-amino acid residues. Digestion of IgG with pepsin generates intact F(ab')$_2$ fragments. Immobilized pepsin gel is washed with digestion buffer; 20 mM sodium acetate, pH 4.5. A solution of purified IgG at 10 mg/ml is added to the immobilized pepsin gel and incubated at 37° C. for 2 hours. The reaction is neutralized by the addition of 10 mM Tris-HCl, pH 7.5 and centrifuged to pellet the gel. The supernatant liquid is collected and applied to an immobilized protein A column, as described above, to separate the F(ab')$_2$ fragments from the Fc and undigested IgG. The pooled F(ab')$_2$ is dialyzed against 10 mM sodium phosphate, 0.15 M NaCl, pH 7.2 and stored at 4° C. The quantity of pooled, eluted F(ab')$^2$ is measured by peak area absorbance at 280 nm.

The purified F(ab')$_2$ fragments at a concentration of 10 mg/ml are reduced at 37° C. for 1 hour in a buffer of 10 mM sodium phosphate, 0.15 M NaCl, 10 mM 2-mercaptoethylamine, 5 mM EDTA, pH 6.0. The Fab' fragments are separated from unsplit F(ab')$_2$ fragments and concentrated by application to a Sephadex G-25 column ($M_r$=46,000–58,000). The pooled Fab' fragments are dialyzed against 10 mM sodium phosphate, 0.15 M NaCl, pH 7.2. The reduced Fab' fragments are diluted to 100 µg/ml and applied onto the bioreactive patches containing exposed aminoreactive functional groups using a computer-aided, capillary-based microdispensing system (for antibody immobilization procedures, see Dammer et al., *Biophys. J.*, 70:2437–2441, 1996). After an immobilization period of 30 minutes at 30° C., the array is rinsed extensively with 10 mM sodium phosphate, 0.15 M NaCl, 5 mM EDTA, pH 7.0.

Transformed human cells grown in culture are collected by low speed centrifugation, briefly washed with ice-cold phosphate-buffered solution (PBS), and then resuspended in ice-cold hypotonic buffer containing DNase/RNase (10 µg/ml each, final concentration) and a mixture of protease inhibitors. Cells are transferred to a microcentrifuge tube, allowed to swell for 5 minutes, and lysed by rapid freezing in liquid nitrogen and thawing in ice-cold water. Cell debris and precipitates are removed by high-speed centrifugation and the supernatant is cleared by passage through a 0.45 µm filter. The cleared lysate is applied to the Fab' fragment array described above and allowed to incubate for 2 hours at 30° C. After binding the array is washed extensively with 10 mM sodium phosphate, 0.15 M NaCl, 5 mM EDTA, pH 7.0. The location and amount of bound proteins are determined by optical detection.

Example 9

Formation and Use of an Array of Immobilized Antibody Fragments to Detect Concentrations of Soluble Proteins Prepared From Cultured Mammalian Cells A combinatorial library of filamentous phage expressing scFv antibody fragments is generated based on the technique of McCafferty and coworkers; McCafferty, et al., *Nature*, 1990, 348:552–554; Winter and Milstein, *Nature*, 1991, 349:293–299. Briefly, mRNA is purified from mouse spleens and used to construct a cDNA library. PCR fragments encoding sequences of the variable heavy and light chain immunoglobulin genes of the mouse are amplified from the prepared cDNA. The amplified PCR products are joined by a linker region of DNA encoding the 15 amino acid peptide (Gly$_4$SerGly$_2$CysGlySerGly$_4$Ser) (SEQ ID NO: 1) and the resulting full-length PCR fragment is cloned into an expression plasmid (pCANTAB 5 E) in which the purification peptide tag (E Tag) has been replaced by a His$_6$ peptide (SEQ ID NO: 2). Electrocompetent TG1 *E. coli* cells are transformed with the expression plasmid by electroporation. The pCANTAB-transformed cells are induced to produced functional filamentous phage expressing scFv fragments by superinfection with M13KO7 helper phage. Cells are grown on glucose-deficient medium containing the antibiotics ampicillin (to select for cells with the phagemid) and kanamycin (to select for cells infected with M13KO7). In the absence of glucose, the lac promoter present on the phagemid is no longer repressed, and synthesis of the scFv-gene 3 fusion begins.

Proteins from a cell lysate are adsorbed to the wells of a 96-well plate. Transformed human cells grown in culture are collected by low speed centrifugation and the cells are briefly washed with ice-cold PBS. The washed cells are then resuspended in ice-cold hypotonic buffer containing DNase/RNase (10 µg/ml each, final concentration) and a mixture of protease inhibitors, allowed to swell for 5 minutes, and lysed by rapid freezing in liquid nitrogen and thawing in ice-cold water. Cell debris and precipitates are removed by high-speed centrifugation and the supernatant is cleared by passage through a 0.45 µm filter. The cleared lysate is diluted to 10 µg/ml in dilution buffer; 20 mM PIPES, 0.15 M NaCl, 0.1% CHAPS, 10%, 5 mM EDTA, 5 mM 2-mercaptoethanol, 2 mM DTT, pH 7.2 and applied to the 96-plate wells. After immobilization for 1 hour at 30° C., the well is washed with the dilution buffer and then incubated with dilution buffer containing 10% nonfat dry milk to block unreacted sites. After the blocking step, the well is washed extensively with the dilution buffer.

Phage expressing displayed antibodies are separated from *E. coli* cells by centrifugation and then precipitated from the supernatant by the addition of 15% w/v PEG 8000, 2.5 M NaCl followed by centrifugation. The purified phage are resuspended in the dilution buffer containing 3% nonfat dry milk and applied to the well containing the immobilized proteins described above, and allowed to bind for 2 hours at 37° C., followed by extensive washing with the binding buffer. Phage are eluted from the well with an elution buffer; 20 mM PIPES, 1 M NaCl, 0.1% CHAPS, 10%, 5 mM EDTA, 5 mM 2-mercaptoethanol, 2 mM DTT, pH 7.2. The well is then extensively washed with purge buffer; 20 mM PIPES, 2.5 M NaCl, 0.1% CHAPS, 10%, 5 mM EDTA, 5 mM 2-mercaptoethanol, 2 mM DTT, pH 7.2. The well is then extensively washed with dilution buffer; 20 mM PIPES, 0.15 M NaCl, 0.1% CHAPS, 10%, 5 mM EDTA, 5 mM 2-mercaptoethanol, 2 mM DTT, pH 7.2. The eluted phage solution is then re-applied to a new well containing adsorbed antigen and the panning enrichment is repeated 4 times. Finally, the phage are eluted from the well with 2M of NaCl in 20 mM PIPES, 0.1% CHAPS, 10%, 5 mM EDTA, 5 mM 2-mercaptoethanol, 2 mM DTT, pH 7.2. Eluates are collected and mixed with log-phase TG1 cells, and grown at 37° C. for 1 hour and then plated onto SOB medium containing ampicillin and glucose and allowed to grow for 12–24 hours.

Individual colonies are picked and arrayed into 96-well 2 ml blocks containing SOB medium and M13KO7 helper phage and grown for 8 hours with shaking at 37° C. The phage are separated from cells by centrifugation and precipitated with PEG/NaCl as described above. Concentrated phage are used to infect HB2151 *E. coli*. *E. coli* TG1 produces a suppressor tRNA which allows readthrough (suppression) of an amber stop codon located between the scFv and phage gene 3 sequences of the pCANTAB 5 E plasmid. Infected HB2151 cells are selected on medium containing ampicillin, glucose, and nalidixic acid. Cells are grown to mid-log and then centrifuged and resuspended in medium lacking glucose and growth continued. Soluble scFv fragments will accumulate in the cell periplasm. A periplasmic extract is prepared from pelleted cells by mild osmotic shock. The soluble scFv released into the supernatant is purified by affinity binding to Ni-NTA activated agarose and eluted with 10 mM EDTA.

The purified scFv antibody fragments are diluted to 100 μg/ml and applied onto the bioreactive patches with exposed aminoreactive groups using a computer-aided, capillary-based microdispensing system. After an immobilization period of 30 minutes at 30° C., the array is rinsed extensively with 10 mM sodium phosphate, 0.15 M NaCl, 5 mM EDTA, pH 7.0.

Transformed human cells grown in culture are collected by low speed centrifugation, briefly washed with ice-cold PBS, and then resuspended in ice-cold hypotonic buffer containing DNase/RNase (10 μg/ml each, final concentration) and mixture of protease inhibitors. Cells are transferred to a microcentrifuge tube, allowed to swell for 5 minutes, and lysed by rapid freezing in liquid nitrogen and thawing in ice-cold water. Cell debris and precipitates are removed by high-speed centrifugation and the supernatant is cleared by passage through a 0.45 μm filter. The cleared lysate is applied to the scFv fragment array described above and allowed to incubate for 2 hours at 30° C. After binding, the array is washed extensively with 0.1 M sodium phosphate, 0.15 M NaCl, 5 mM EDTA pH 7.0. The location and amount of bound proteins are determined by optical detection.

Patterns of binding are established empirically by testing dilutions of a control cell extract. Extracts from experimental cells are diluted to a series of concentrations and then tested against the array. Patterns of protein expression in the experimental cell lysates are compared to protein expression patterns in the control samples to identify proteins with unique expression profiles.

Example 10

Formation and Use of an Array of Immobilized Monoclonal Antibodies to Detect Concentrations of Soluble Proteins Prepared From Cultured Mammalian Cells Collections of monoclonal antibodies are purchased from commercial suppliers as either raw ascities fluid or purified by chromotography over protein A, protein G, or protein L. If from raw ascites fluid, the antibodies are purified using a HiTrap Protein G or HiTrap Protein A column (Pharmacia) as appropriate for the immunoglobulin subclass and species. Prior to chromotography the ascites are diluted with an equal volume of 10 mM sodium phosphate, 0.9% NaCl, pH 7.4 (PBS) and clarified by passage through a 0.22 μm filter. The filtrate is loaded onto the column in PBS and the column is washed with two column volumes of PBS. The antibody is eluted with 100 mM Glycine-HCl, pH 2.7 (for protein G) or 100 mM citric acid, pH 3.0 (for protein A). The eluate is collected into ¹/₁₀ volume 1 M Tris-HCl, pH 8.0. The final pH is 7.5. Fractions containing the antibodies are confirmed by SDS-PAGE and then pooled and dialyzed against PBS.

The different samples of purified antibodies are each diluted to 100 μg/ml. Each different antibody sample is applied to a separate patch of an array of aminoreactive monolayer patches (see Example 4, above) using a computer-aided, capillary-based microdispensing system. After an immobilization period of 30 minutes at 30° C., the array is rinsed extensively with 10 mM sodium phosphate, 0.15 M NaCl, 5 mM EDTA, pH 7.0.

Transformed human cells grown in culture are collected by low speed centrifugation, briefly washed with ice-cold PBS, and resuspended in ice-cold hypotonic buffer containing Dnase/Rnase (10 μg/ml each, final concentration) and a mixture of protease inhibitors. Cells are transferred to a microcentrifuge tube, allowed to swell for 5 minutes, and lysed by rapid freezing in liquid nitrogen and thawing in ice-cold water. Cell debris and precipitates are removed by high-speed centrifugation and the supernatant is cleared by passage through a 0.45 μm filter. The cleared lysate is applied to the monoclonal antibody array described above and allowed to incubate for 2 hours at 30° C. After binding the array is washed extensively as in Example 9, above. The location and amount of bound proteins are determined by optical detection.

All documents cited in the above specification are herein incorporated by reference. In addition, the co-pending U.S. patent application "Arrays of Protein-Capture Agents and Methods of Use Thereof", filed on Jul. 14, 1999, with the identifier 24406–0006, for the inventors Peter Wagner, Steffen Nock, Dana Ault-Riche, and Christian Itin, is herein incorporated by reference in its entirety. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An array device comprising:

a substrate defining a surface, and an array of discrete array-regions over the surface;

an ordered hydrophobic-monolayer formed of alkyl-chains having alkyl-chain proximal ends which are chemisorbed or physisorbed to said surface, and opposite alkyl-chain distal ends;

a hydrophilic-monolayer formed from hydrophilic-chains, each having a hydrophilic-chain proximal end by which each hydrophilic-chain is covalently linked to an alkyl-chain distal end, and an opposite hydrophilic-chain distal end, said ordered hydrophobic-monolayer and said hydrophilic-monolayer being effective in combination to resist non-specific protein binding; and, a plurality of protein-immobilizing groups covalently attached to a selected fraction of said hydrophilic-chains' distal ends within said array-regions, such that application of one or more selected proteins to selected array-regions is effective to form an array of protein-regions, each having a selected surface concentration of a selected protein carried in and displayed on said hydrophilic-monolayer, and separated from one another by border-regions effective to resist non-specific protein binding.

2. The device of claim 1, wherein said hydrophobic polymer chains are hydrocarbon chains of length 8–22 carbons.

3. The device of claim 1, wherein said hydrophilic polymer chains are polyethyleneglycol chains.

* * * * *

SEQUENCE LISTING

<160> NUMBER OF SEQ ID NOS: 6

<210> SEQ ID NO 1
<211> LENGTH: 6
<212> TYPE: PRT
<213> ORGANISM: Artificial Sequence
<220> FEATURE:

```
<221> NAME/KEY: MOD_RES
<222> LOCATION: (1)
<223> OTHER INFORMATION: N-dansyl
<220> FEATURE:
<223> OTHER INFORMATION: Description of Artificial Sequence: labeled
      peptide aldehyde inhibitor of caspase
<220> FEATURE:
<221> NAME/KEY: MOD_RES
<222> LOCATION: (6)
<223> OTHER INFORMATION: aldehyde

<400> SEQUENCE: 1

Ser Ser Asp Glu Val Asp
 1               5

<210> SEQ ID NO 2
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: N-dansyl
<220> FEATURE:
<223> OTHER INFORMATION: Description of Artificial Sequence: labeled
      peptide aldehyde inhibitor of caspase
<220> FEATURE:
<221> NAME/KEY: MOD_RES
<222> LOCATION: (7)
<223> OTHER INFORMATION: aldehyde

<400> SEQUENCE: 2

Ser Ser Val Asp Val Ala Asp
 1               5

<210> SEQ ID NO 3
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: N-dansyl
<220> FEATURE:
<223> OTHER INFORMATION: Description of Artificial Sequence: labeled
      peptide aldehyde inhibitor of caspase
<220> FEATURE:
<221> NAME/KEY: MOD_RES
<222> LOCATION: (6)
<223> OTHER INFORMATION: aldehyde

<400> SEQUENCE: 3

Ser Ser Val Gln Ile Asp
 1               5

<210> SEQ ID NO 4
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: N-acetyl
<220> FEATURE:
<223> OTHER INFORMATION: Description of Artificial Sequence:  peptide
      aldehyde inhibitor of caspase
<220> FEATURE:
<221> NAME/KEY: MOD_RES
<222> LOCATION: (4)
<223> OTHER INFORMATION: aldehyde

<400> SEQUENCE: 4
```

-continued

```
Asp Glu Val Asp
  1

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: linker

<400> SEQUENCE: 5

Gly Gly Gly Gly Ser Gly Gly Cys Gly Ser Gly Gly Gly Gly Ser
  1               5                  10                  15

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: histidine
      tag

<400> SEQUENCE: 6

His His His His His His
  1               5
```